US012703696B2

(12) United States Patent
Boehm et al.

(10) Patent No.: US 12,703,696 B2
(45) **Date of Patent: *Aug. 11, 2026**

(54) DIACYLGLYCEROL ACYL TRANSFERASE 2 INHIBITORS

(71) Applicant: Pfizer Inc., New York, NY (US)

(72) Inventors: Markus Boehm, Mansfield, MA (US); Shawn Cabral, Groton, CT (US); Matthew S. Dowling, Old Lyme, CT (US); Kentaro Futatsugi, Qunicy, MA (US); Kim Huard, Berkeley, CA (US); Esther Cheng Yin Lee, Newton, MA (US); Allyn T. Londregan, Barrington, RI (US); Jana Polivkova, Mystic, CT (US); David A. Price, Concord, MA (US); Qifang Li, Stonington, CT (US)

(73) Assignee: Pfizer Inc., New York, NY (US)

( * ) Notice: Subject to any disclaimer, the term of this patent is extended or adjusted under 35 U.S.C. 154(b) by 148 days.

This patent is subject to a terminal disclaimer.

(21) Appl. No.: 18/520,638

(22) Filed: Nov. 28, 2023

(65) Prior Publication Data

US 2024/0140937 A1 May 2, 2024

Related U.S. Application Data

(63) Continuation of application No. 17/345,064, filed on Jun. 11, 2021, now Pat. No. 11,866,425, which is a continuation of application No. 16/793,441, filed on Feb. 18, 2020, now Pat. No. 11,034,678, which is a continuation of application No. 15/977,238, filed on May 11, 2018, now abandoned, which is a continuation of application No. 15/674,914, filed on Aug. 11, 2017, now Pat. No. 10,071,992.

(60) Provisional application No. 62/377,137, filed on Aug. 19, 2016.

(51) Int. Cl.

| | |
|---|---|
| ***C07D 405/14*** | (2006.01) |
| ***A61K 31/506*** | (2006.01) |
| ***A61K 45/06*** | (2006.01) |
| ***C07D 401/14*** | (2006.01) |
| ***C07D 409/14*** | (2006.01) |
| *A61P 3/00* | (2006.01) |
| *A61P 3/06* | (2006.01) |
| *A61P 3/10* | (2006.01) |

(52) U.S. Cl.

CPC .......... *C07D 405/14* (2013.01); *A61K 31/506* (2013.01); *A61K 45/06* (2013.01); *C07D 401/14* (2013.01); *C07D 409/14* (2013.01); *A61P 3/00* (2018.01); *A61P 3/06* (2018.01); *A61P 3/10* (2018.01); *C07B 2200/13* (2013.01)

(58) Field of Classification Search

None

See application file for complete search history.

(56) References Cited

U.S. PATENT DOCUMENTS

| | | | |
|---|---|---|---|
| 6,818,658 B2 | 11/2004 | Ujjaninwalla et al. | |
| 9,181,223 B2 | 11/2015 | Kaufman et al. | |
| 10,071,992 B2 | 9/2018 | Boehm et al. | |
| 11,034,678 B2 | 6/2021 | Boehm et al. | |
| 11,866,425 B2 * | 1/2024 | Boehm .................. | A61P 25/00 |
| 2005/0267100 A1 | 12/2005 | Elliott et al. | |
| 2006/0178501 A1 | 8/2006 | Summers et al. | |
| 2015/0259323 A1 | 9/2015 | Cabral et al. | |

FOREIGN PATENT DOCUMENTS

| | | |
|---|---|---|
| RU | 2014124953 | 11/2012 |
| RU | 201514717 | 3/2014 |
| WO | 2003072197 | 9/2003 |
| WO | 2005116014 | 12/2005 |
| WO | 2005116034 | 12/2005 |
| WO | 2007122482 | 11/2007 |
| WO | 2008065508 | 6/2008 |
| WO | 2009016462 | 2/2009 |
| WO | 2009144555 | 12/2009 |
| WO | 2010013161 | 2/2010 |
| WO | 2010077861 A1 | 7/2010 |
| WO | 2010086820 | 8/2010 |
| WO | 2010103437 | 9/2010 |
| WO | 2010103438 | 9/2010 |
| WO | 2010106457 | 9/2010 |
| WO | 2010128414 | 11/2010 |
| WO | 2010128425 | 11/2010 |
| WO | 2010140092 | 12/2010 |
| WO | 2011005611 | 1/2011 |
| WO | 2013079493 | 6/2013 |
| WO | 2013137628 | 9/2013 |
| WO | 2013150416 | 10/2013 |
| WO | 2014145025 | 9/2014 |
| WO | 2015077299 | 5/2015 |
| WO | 2015140658 | 9/2015 |

(Continued)

OTHER PUBLICATIONS

Buhman et al., "DGAT1 is Not Essential for Intestinal Triacylglycerol Absorption or Chylomicron Synthesis", J. Biol. Chem., (2002), pp. 25474-25479, 277(28).

Carpino et al., "Diabetes area participation analysis: a review of companies and targets described in the 2008-2010 patent literature", Expert Opinion on Therapeutic Patents, (2010), pp. 1627-1651, 20(12).

Chilean Patent Application No. 201900406 Examination Report, Mar. 17, 2020, 10 pages.

Choi et al., "Increased very low density lipoprotein (VLDL) secretion, hepatic steatosis, and insulin resistance", Trends in Endocrinology and Metabolism, (2011), pp. 353-363, 22(9).

(Continued)

*Primary Examiner* — Brian J Davis

(74) *Attorney, Agent, or Firm* — Hamilton, Brook, Smith & Reynolds, P.C.

(57) ABSTRACT

Compounds of Formula I that inhibit the activity of the diacylglycerol acyltransferase 2 (DGAT2) and their uses in the treatment of diseases linked thereto in animals are described herein.

15 Claims, 2 Drawing Sheets

(56) References Cited

FOREIGN PATENT DOCUMENTS

| | | |
|---|---|---|
| WO | 2016036633 | 3/2016 |
| WO | 2016036636 | 3/2016 |
| WO | 2016036638 | 3/2016 |
| WO | 2009144554 | 12/2019 |

OTHER PUBLICATIONS

Choi et al., "Suppression of Diacylglycerol Acyltransferase-2 (DGAT2), but Not DGAT1, with Antisense Oligonucleotides Reverses Diet-Induced Hepatic Steatosis and Insulin Resistance", J. Biol. Chem., (2007), pp. 22678-22688, 282(31).

Coleman et al., "Mammalian Triacylglycerol Metabolism: Synthesis, Lipolysis, and Signaling", Chemical Reviews, (2011), pp. 6359-6389, 111(10).

Erion et al., "Diacylglycerol-mediated insulin resistance", Nature Medicine, (2010), pp. 400-402, 16(4).

Futatsugi et al., Discovery and Optimization of Imidazopyridine-Based Inhibitors of Diacylglycerol Acyltransferase 2 (DGAT2), J. Med. Chem., (2015), pp. 7173-7185, 58(18).

Futatsugi et al., "Small structural changes of the imidazopyridine diacylglycerol acyltransferase 2 (DGAT2) inhibitors produce an improved safety profile", Med Chem Commun., (2017), pp. 771-779, vol. 8.

Hazlehurst, et al., "Non-alcohlic fatty liver disease and diabetes", Metabolism Clinical and Experimental, 2016, pp. 1096-1108.

Imbriglio et al., "Discovery and Pharmacology of a Novel Class of Diacylglycerol Acyltransferase 2 Inhibitors", J. Med. Chem., (2015), pp. 9345-9353, 58(23).

Jones et al., "The Emergence of GPR119 Agonists as Anti-Diabetic Agents", Annual Reports in Medicinal Chemistry, (2009), pp. 149-170, vol. 44.

Kim et al., "Discovery of a Novel Class of Diacylglycerol Acyltransferase 2 Inhibitors with a 1H-Pyrrolo[2,3-b]Pyridine Core", Biol. Pharm. Bull., (2014), pp. 1655-1660, 37(10).

Kim et al., "Identification and Validation of a Selective Small Molecule Inhibitor Targeting the Diacylglycerol Acyltransferase 2 Activity", Biol. Pharm. Bull., (2013), pp. 1167-1173, 36(7).

Lee et al., "Discovery of indolyl acrylamide derivatives as human diacylglycerol acyltransferase-2 selective inhibitors", Organic & Biomolecular Chemistry, (2013), pp. 849-858, 11(5).

Lee et al., "Intestine-specific expression of acyl CoA:diacylglycerol acyltransferase 1 reverse resistance to diet-induced hepatic steatosis and obesity in Dgat1 −/− mice", Journal of Lipid Research, (2010), pp. 1770-1780, 51(7).

Liu et al., "Knockdown of Acyl-CoA:diacylglycerol acyltransferase 2 with antisense oligonucleotide reduces VLDL Tg and ApoB secretion in mice", Biochimica et Biophysica Acta, (2008), pp. 97-104, 1781(3).

Medina et al., "GPR40 (FFAR1) Modulators", Annual Reports in Medicinal Chemistry, (2008), pp. 75-85, vol. 43.

Oshiro, et al., Acyltransferase inhibitors: a patent review (2019 to present) Expert Opinion on Therapeutic Patents, 2015, pp. 145-158, 25(2).

Paletas, "Non alcoholic fatty liver disease and metabolic syndrome", Hippokratia, 2009, pp. 9-19, 13(1).

Qi et al., "The use of stable isotope-labeled glycerol and oleic acid to differentiate the hepatic functions of DGAT2 and -2", Journal of Lipid Research, (2012), pp. 1106-1116, 53(6).

Russian Application No. 2019104413, filed Aug. 9, 2017, Search Report dated Nov. 18, 2019, mailed Nov. 25, 2019, 2 pages.

Smith et al., "Obesity resistance and multiple mechanisms of triglyceride synthesis in mice lacking Dgat", Nature Genetics, (2000), pp. 87-90, 25(1).

St. Pierre et al., "Low-Density Lipoprotein Subfractions and the Long-Term Risk of Ischemic Heart Disease in Men", Arterioscler Throm Vasc. Biol., (2005), pp. 553-559, 25(3).

Stone et al., "Lipopenia and Skin Barrier Abnormalities in DGAT2-deficient mice", J. Biol. Chem., (2004), pp. 11767-11776, 279(12).

Wurie et al., "Diacylglycerol acyltransferase 2 acts upstream of diacylglycerol acyltransferase 1 and utilizes nascent diglycerides and de novo synthesized fatty acids in HepG2 cells", FEBS Journal, (2012), pp. 3033-3047, 279(17).

Yen et al., "DGAT enzymes and triacylglycerol biosynthesis", Journal of Lipid Research, (2008), pp. 2283-2301, 49 (11).

Yu et al., "Antisense Oligonucleotide Reduction of DGAT2 Expression Improves Hepatic Steatosis and Hyperlipidemia in Obese Mice", Hepatology, (2005), pp. 362-371, 42(2).

Zhang et al., "PTP1B as a drug target: recent developments in PTP1B inhibitor discovery", Drug Discovery Today, (2007), pp. 373-381, 12(9/10).

Zhong, "TGR5 as a Therapeutic Target for Treating Obesity", Current Topics in Medicinal Chemistry, (2010), pp. 386-396, vol. 10.

* cited by examiner

DIACYLGLYCEROL ACYL TRANSFERASE 2 INHIBITORS

CROSS REFERENCE TO PRIOR APPLICATIONS

This application is a CONTINUATION of U.S. application Ser. No. 17/345,064, filed Jun. 11, 2021 which claims the benefit of U.S. CONTINUATION application Ser. No. 16/793,441, filed Feb. 18, 2020, which claims the benefit of U.S. CONTINUATION application Ser. No. 15/977,238 filed May 11, 2018, which claims the benefit of U.S. CONTINUATION application Ser. No. 15/674,914, filed Aug. 11, 2017, which claims the benefit of U.S. Provisional Application Ser. No. 62/377,137, filed Aug. 19, 2016 under 35 USC 119(e), the disclosures of which are hereby incorporated in their entirety.

FIELD OF THE INVENTION

The present invention relates to new pharmaceutical compounds, pharmaceutical compositions containing these compounds, and their use to inhibit the activity of the diacylglycerol acyltransferase 2 (DGAT2).

BACKGROUND OF THE INVENTION

Triglycerides or triacylglycerols (TAG) represent a major form of energy storage in mammals. TAG's are formed by the sequential esterification of glycerol with three fatty acids of varying chain lengths and degrees of saturation (1). TAG synthesized in the intestine or liver are packaged into chylomicrons or very low-density lipoprotein (VLDL), respectively, and exported to peripheral tissues where they are hydrolysed to their constituent fatty acids and glycerol by lipoprotein lipase (LPL). The resultant non-esterified fatty acids (NEFA) can either be metabolised further to produce energy or reesterified and stored.

Under normal physiological conditions, the energy-dense TAG remains sequestered in various adipose depots until there is a demand for its release, whereupon, it is hydrolyzed to glycerol and free fatty acids which are then released into the blood stream. This process is tightly regulated by the opposing actions of insulin and hormones such as catecholamines which promote the deposition and mobilization of TAG stores under various physiological conditions. In the post-prandial setting, insulin acts to inhibit lipolysis, thereby, restraining the release of energy in the form of NEFA and ensuring the appropriate storage of dietary lipids in adipose depots. However, in patients with type 2 diabetes, the ability of insulin to suppress lipolysis is ameliorated and NEFA flux from adipocytes is inappropriately elevated. This, in turn, results in increased delivery of lipid to tissues such as muscle and liver. In the absence of energetic demand the TAG and other lipid metabolites, such as diacylglycerol (DAG) can accumulate and cause a loss of insulin sensitivity (2). Insulin resistance in muscle is characterized by reduced glucose uptake and glycogen storage, whilst in the liver, loss of insulin signaling gives rise to dysregulated glucose output and over-production of TAG-rich VLDL, a hallmark of type 2 diabetes (3). Elevated secretion of TAG-enriched VLDL, so called VLDL1 particles, is thought to stimulate the production of small, dense low-density lipoprotein (sdLDL), a proatherogenic subfraction of LDL that is associated with elevated risk of coronary heart disease (4).

Diacylglycerol acyltransferases (DGAT) catalyze the terminal step in TAG synthesis, specifically, the esterification of a fatty acid with diacylglycerol resulting in the formation of TAG. In mammals, two DGAT enzymes (DGAT1 and DGAT2) have been characterized. Although these enzymes catalyze the same enzymatic reaction their respective amino acid sequences are unrelated and they occupy distinct gene families. Mice harboring a disruption in the gene encoding DGAT1 are resistant to diet-induced obesity and have elevated energy expenditure and activity (5). Dgat1−/− mice exhibit dysregulated postaborpative release of chylomicrons and accumulate lipid in the enterocytes (6). The metabolically favorable phenotype observed in these mice is suggested to be driven by loss of DGAT1 expression in the intestine (7). Importantly, despite a defect in lactation in female Dgat1−/− mice, these animals retain the capacity to synthesize TAG suggesting the existence of additional DGAT enzymes. This observation and the isolation of a second DGAT from the fungus *Mortierella rammaniana* led to the identification and characterization of DGAT2 (8).

DGAT2 is highly expressed in liver and adipose, and unlike DGAT1, exhibits exquisite substrate specificity for DAG (8). Deletion of the DGAT2 gene in rodents results in defective intraunterine growth, severe lipemia, impaired skin barrier function, and early post-natal death (9). Due to the lethality caused by loss of DGAT2, much of our understanding of the physiological role of DGAT2 derives from studies performed with antisense oligonucleotides (ASO) in rodent models of metabolic disease. In this setting, inhibition of hepatic DGAT2 resulted in improvements in plasma lipoprotein profile (decrease in total cholesterol and TAG) and a reduction of hepatic lipid burden which was accompanied by improved insulin sensitivity and whole-body glucose control (10-12). Although the molecular mechanisms underlying these observations are not fully elucidated, it is clear that suppression of DGAT2 results in a down-regulation of the expression of multiple genes encoding proteins involved in lipogensis, including sterol regulatory element-binding proteins 1c (SREBP1c) and stearoyl CoA-desaturase 1 (SCD1) (11, 12). In parallel, oxidative pathways are induced as evidenced by increased expression of genes such as carnitine palmitoyl transferase 1 (CPT1) (11). The net result of these changes is to decrease the levels of hepatic DAG and TAG lipid which, in turn, leads to improved insulin responsiveness in the liver. Furthermore, DGAT2 inhibition suppresses hepatic VLDL TAG secretion and reduction in circulating cholesterol levels. Finally, plasma apolipoprotein B (APOB) levels were suppressed, possibly due to decreased supply of TAG for lipidation of the newly synthesized APOB protein (10, 12). The beneficial effects of DGAT2 inhibition on both glycemic control and plasma cholesterol profile suggest that this target might be valuable in the treatment of metabolic disease (11). In addition, the observation that suppression of DGAT2 activity results in reduced hepatic lipid accumulation suggests that inhibitors of this enzyme might have utility in the treatment of non-alcoholic steatohepatitis (NASH), a highly prevalent liver disease characterized by the deposition of excess fat in the liver.

In recent years, several small molecule inhbitors of DGAT2 have been reported in literature (13-19) and patent applications (WO2013150416, WO2013137628, US20150259323, WO2015077299, WO2016036633, WO2016036638, WO2016036636).

1. Coleman, R. A., and D. G. Mashek. 2011. *Chem Rev* 111: 6359-6386.
2. Erion, D. M., and G. I. Shulman. 2010. *Nat Med* 16: 400-402.

3 Choi, S. H., and H. N. Ginsberg. 2011. *Trends Endocrinol Metab* 22: 353-363.
4. St-Pierre, A. C. et. al. 2005. *Arterioscler Thromb Vasc Biol* 25: 553-559.
5. Smith, S. J. et. al. 2000. *Nat Genet* 25: 87-90.
6. Buhman, K. K. et. al. 2002. *J Biol Chem* 277: 25474-25479.
7. Lee, B., A. M. et. al. 2010. *J Lipid Res* 51: 1770-1780.
8. Yen, C. L. et. al. 2008. *J Lipid Res* 49: 2283-2301.
9. Stone, S. J. et. al. 2004. *J Biol Chem* 279: 11767-11776.
10. Liu, Y. et. al. 2008. *Biochim Biophys Acta* 1781: 97-104.
11. Choi, C. S. et. al. 2007. *J Biol Chem* 282: 22678-22688.
12. Yu, X. X. et. al. 2005. *Hepatology* 42: 362-371.
13. Qi, J. et. al. *J. Lipid. Res.* 2012, 53 (6), 1106-16.
14. Wurie, H. R. et. al. *FEBS. J.* 2012, 279 (17), 3033-47;
15. Kim, M. O. et. al. *Biol. Pharm. Bull.* 2013, 36 (7), 1167-73
16 Lee, K. et. al. Org. *Biomol. Chem.* 2013, 11 (5), 849-58
17 Kim, M. O. et. al. *Biol. Pharm. Bull.* 2014, 37 (10), 1655-1660.
18. Futatsugi, K. et. al. *J Med Chem* 2015, 58 (18), 7173-85.
19. Imbriglio, J. E. et. al. *J. Med. Chem.* 2015, 58 (23), 9345-9353.

SUMMARY OF THE INVENTION

The present application is directed at compounds of Formula (I) and (Ia)

(I)

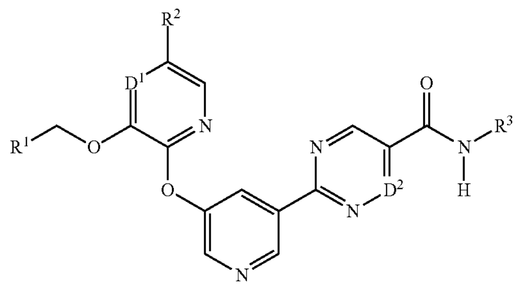

(Ia)

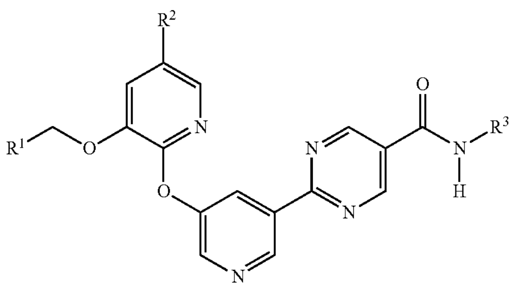

wherein $D^1$ and $D^2$ are each independently N or CH;

$R^1$ is H, or $(C_1-C_2)$alkyl optionally substituted with one or two substituents each independently selected from fluoro and $(C_3-C_6)$cycloalkyl;

$R^2$ is H or fluoro;

$R^3$ is

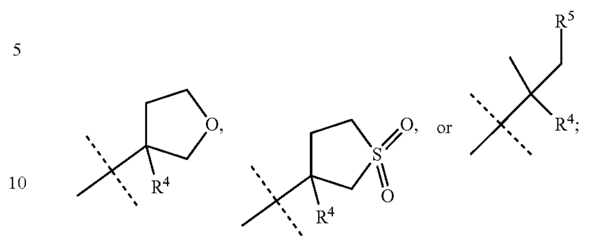

$R^4$ is H, cyano, or $(C_1-C_4)$alkyl optionally substituted with one or two substituents each independently selected from —OH and $—S(O)_2R^6$;

$R^5$ is H or —OH; and $R^6$ is $(C_1-C_4)$alkyl;

or a pharmaceutically acceptable salt thereof.

The present invention is also directed at a crystal comprising a compound having the structure:

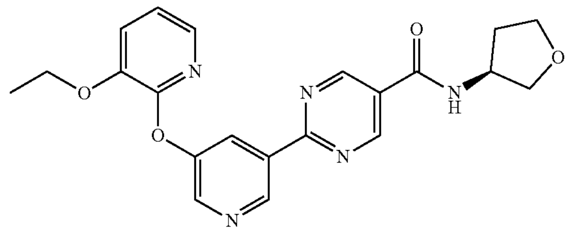 [SMILES: CCOc1cccnc1Oc1cncc(-c2ncc(C(=O)N[C@H]3CCOC3)cn2)c1]

or a pharmaceutically acceptable salt thereof.

The present invention is also directed at pharmaceutical compositions that include a compound of Formula (I) or (Ia) or a pharmaceutically acceptable salt of said compound, present in a therapeutically effective amount, in admixture with at least one pharmaceutically acceptable excipient.

Furthermore, the present invention is directed at pharmaceutical compositions that include a compound of Formula (I) or (Ia) or a pharmaceutically acceptable salt of said compound, present in a therapeutically effective amount, in admixture with at least one pharmaceutically acceptable excipient and further including at least one additional pharmaceutical agent selected from the group consisting of an anti-inflammatory agent, an anti-diabetic agent, and a cholesterol/lipid modulating agent.

In another embodiment, the method of the present invention is for the treatment of hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, transient ischemic attacks, stroke, vascular restenosis, hyperglycemia, hyperinsulinemia, hypertrygliceridemia, insulin resistance, impaired glucose metabolism, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), or non-alcoholic fatty liver disease (NAFLD), in humans.

In another embodiment, the method reduces portal hypertension, hepatic protein synthetic capability, hyperbilirubinemia, or encephalopathy.

The present invention is also directed at a method for the treatment of reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a human in need of such reductiondiabetes comprising the administration of an effective an effective amount of a compound of Formula (I) or (Ia) or a pharmaceutically acceptable salt of said compound or a pharmaceutically acceptable salt of said compound to a patient in need thereof.

The present invention is also directed at a method for treating fatty liver, nonalcoholic fatty liver disease, nonalcoholic steatohepatitis, nonalcoholic steatohepatitis with liver fibrosis, nonalcoholic steatohepotitis with cirrhosis, or nonalcoholic steatohepatitis with cirrhosis and hepatocellular carcinoma metabolic or metabolic-related disease, condition or disorder in humans comprising the step of administering to a human in need of such treatment comprising the step of administering to a patient a therapeutically effective amount of a compound of Formula (I) or (Ia) or a pharmaceutically acceptable salt of said compound or a pharmaceutically acceptable salt of said compound.

The present invention is also directed at a method for treating fatty liver, nonalcoholic fatty liver disease, nonalcoholic steatohepatitis, nonalcoholic steatohepatitis with liver fibrosis, nonalcoholic steatohepotitis with cirrhosis, or nonalcoholic steatohepatitis with cirrhosis and hepatocellular carcinoma metabolic or metabolic-related disease, condition or disorder in humans comprising the step of administering to a human in need of such treatment comprising the step of administering to a patient in need of such treatment a therapeutically effective amount of two separate pharmaceutical compositions comprising (i) a first composition that includes a compound of Formula (I) or (Ia) or a pharmaceutically acceptable salt of said compound, present in a therapeutically effective amount, in admixture with at least one pharmaceutically acceptable excipient; and (ii) a second composition comprising at least one additional pharmaceutical agent selected from the group consisting of an anti-inflammatory agent, an anti-diabetic agent, and a cholesterol/lipid modulating agent and an anti-diabetic agent, and at least one pharmaceutically acceptable excipient.

It is to be understood that both the foregoing general description and the following detailed description are exemplary and explanatory only and are not restrictive of the invention, as claimed.

DETAILED DESCRIPTION OF THE INVENTION

Figure 1:
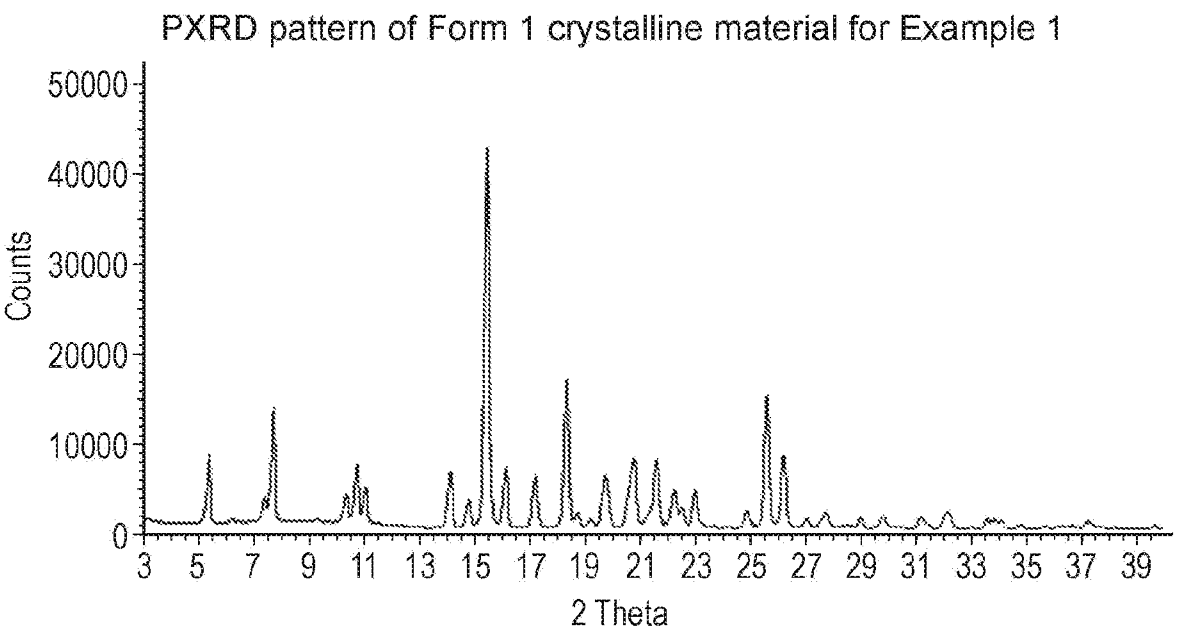
FIG. 1 is a characteristic x-ray powder diffraction pattern showing crystalline Form 1 of Example 1 (Vertical Axis: Intensity (CPS); Horizontal Axis: Two theta (degrees)).

The present invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

"Compounds" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the compounds of the present invention include but are not limited to those having a carboxyl moiety wherein the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N, N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

As used herein, an arrowhead, "/" or wavy line,

denotes a point of attachment of a substituent to another group.

By "alkyl" is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, isobutyl, pentyl, isopentyl, neopentyl, tertiary pentyl, 1-methylbutyl, 2-methylbutyl, 3-methylbutyl, hexyl, isohexyl, heptyl and octyl.

The term "aryl" means a carbocyclic aromatic system containing one, two or three rings wherein such rings may be fused. If the rings are fused, one of the rings must be fully unsaturated and the fused ring(s) may be fully saturated, partially unsaturated or fully unsaturated. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indanyl, biphenyl, benzo[b][1,4]oxazin-3(4H)-onyl, 2,3-dihydro-1H indenyl, and 1,2,3,4-tetrahydronaphthalenyl.

"Cycloalkyl" refers to a nonaromatic ring that is fully hydrogenated having one, two or three rings wherein such rings may be fused, wherein fused is defined above. Cycloalkyl also includes bicyclic structures that may be bridged or spirocyclic in nature with each individual ring within the bicycle varying from 3-8 atoms. Examples of such carbocyclic rings include cyclopropyl, cyclobutyl, cyclopentyl, and cyclohexyl.

The term "heteroaryl" means an aromatic carbocyclic system containing one, two, three or four heteroatoms selected independently from oxygen, nitrogen and sulfur and having one, two or three rings wherein such rings may be fused, wherein fused is defined above. The term "heteroaryl" includes but is not limited to furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridiazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

"Patient" refers to warm blooded animals such as, for example, guinea pigs, mice, rats, gerbils, cats, rabbits, dogs, cattle, goats, sheep, horses, monkeys, chimpanzees, and humans.

By "pharmaceutically acceptable" is meant that the substance or composition must be compatible chemically and/or toxicologically, with the other ingredients comprising a formulation, and/or the mammal being treated therewith.

As used herein, the expressions "reaction-inert solvent" and "inert solvent" refer to a solvent or a mixture thereof which does not interact with starting materials, reagents, intermediates or products in a manner which adversely affects the yield of the desired product.

As used herein, the term "selectivity" or "selective" refers to a greater effect of a compound in a first assay, compared to the effect of the same compound in a second assay. For example, in "gut selective" compounds, the first assay is for the half life of the compound in the intestine and the second assay is for the half life of the compound in the liver.

"Therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", "treat" or "treatment" as used herein embraces both preventative, i.e., prophylactic, and palliative treatment, i.e., relieve, alleviate, or slow the progression of the patient's disease (or condition) or any tissue damage associated with the disease.

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds of the present invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the present invention possess one or more stereogenic centers and no stereochemistry is given in the name or structure, it is understood that the name or structure is intended to encompass all forms of the compound, including the racemic form.

The compounds of this invention may contain olefin-like double bonds. When such bonds are present, the compounds of the invention exist as cis and trans configurations and as mixtures thereof. The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations.

Valence tautomers include interconversions by reorganization of some of the bonding electrons.

Included within the scope of the claimed compounds present invention are all stereoisomers, geometric isomers and tautomeric forms of the compounds of Formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically-labelled compounds of Formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$, $^{124}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy. p Isotopically-labelled compounds of Formula (I) can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately treating the compound with a suitable organic or inorganic acid or base and isolating the salt thus formed. The acids which are used to prepare the pharmaceutically acceptable acid addition salts of the aforementioned base compounds of this invention are those which form non-toxic acid addition salts, (i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, naphthylate, mesylate, glucoheptonate, lactobionate, laurylsulphonate, hexafluorophosphate, benzene sulfonate, tosylate, formate, trifluoroacetate, oxalate, besylate, palmitiate, pamoate, malonate, stearate, laurate, malate, borate, p-toluenesulfonate and pamoate (i.e., 1,1'-methylene-bis-(2-hydroxy-3-naphthoate)) salts.

The invention also relates to base addition salts of the compounds of the present invention. The chemical bases that may be used as reagents to prepare pharmaceutically acceptable base salts of those compounds of the present invention that are acidic in nature are those that form non-toxic base salts with such compounds. Such non-toxic base salts include, but are not limited to those derived from such pharmacologically acceptable cations such as alkali metal cations (e.g., lithium, potassium and sodium) and alkaline earth metal cations (e.g., calcium and magnesium), ammonium or water-soluble amine addition salts such as N-methylglucamine-(meglumine), tetramethylammonium, tetraethylammonium, methylamine, dimethylamine, trimethylamine, triethylamine, ethylamine, and the lower alkanolammonium and other base salts of pharmaceutically acceptable organic amines. See e.g. Berge, et al. *J. Pharm. Sci.* 66, 1-19 (1977).

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

In one embodiment, $R^3$ is

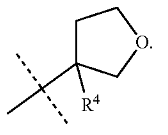

In another embodiment, $R^3$ is

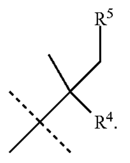

In a further embodiment, $R^1$ is methyl.

In yet another embodiment, $R^4$ is H, $-CH_2OH$, or cyano.

In another embodiment, the compound is (S)-2-(5-((3-Ethoxy-5-fluoropyridin-2-yl)oxy)pyridin-3-yl)-N-(tetrahydrofuran-3-yl)pyrimidine-5-carboxamide;

N-(2-cyanopropan-2-yl)-2-(5-((3-ethoxypyridin-2-yl)oxy)pyridin-3-yl)pyrimidine-5-carboxamide;

2-(5-((3-ethoxypyridin-2-yl)oxy)pyridin-3-yl)-N-(3-methyl-1,1-dioxidotetrahydrothiophen-3-yl)pyrimidine-5-carboxamide;

2-(5-((3-ethoxypyridin-2-yl)oxy)pyridin-3-yl)-N-(1-hydroxy-2-methylpropan-2-yl)pyrimidine-5-carboxamide;

(S)-2-(5-((3-ethoxypyridin-2-yl)oxy)pyridin-3-yl)-N-(tetrahydrofuran-3-yl)pyrimidine-5-carboxamide;

(S)-2-(5-((3-ethoxypyridin-2-yl)oxy)pyridin-3-yl)-N-(3-(hydroxymethyl)tetrahydrofuran-3-yl)pyrimidine-5-carboxamide;

(R)-2-(5-((3-ethoxypyridin-2-yl)oxy)pyridin-3-yl)-N-(3-(hydroxymethyl)tetrahydrofuran-3-yl)pyrimidine-5-carboxamide;

2-(5-((3-ethoxypyridin-2-yl)oxy)pyridin-3-yl)-N-(2-methyl-1-(methylsulfonyl)propan-2-yl)pyrimidine-5-carboxamide;

(S)-2-(5-((3-(2-fluoroethoxy)pyridin-2-yl)oxy)pyridin-3-yl)-N-(tetrahydrofuran-3-yl)pyrimidine-5-carboxamide;

3-(5-((3-ethoxypyridin-2-yl)oxy)pyridin-3-yl)-N-(1-hydroxy-2-methylpropan-2-yl)-1,2,4-triazine-6-carboxamide;

N-(1,3-dihydroxy-2-methylpropan-2-yl)-2-(5-((3-ethoxypyridin-2-yl)oxy)pyridin-3-yl)pyrimidine-5-carboxamide;

(S)-3-(5-((3-ethoxypyridin-2-yl)oxy)pyridin-3-yl)-N-(tetrahydrofuran-3-yl)-1,2,4-triazine-6-carboxamide;

N-(1,1-dioxidotetrahydrothiophen-3-yl)-2-(5-((3-ethoxypyridin-2-yl)oxy)pyridin-3-yl)pyrimidine-5-carboxamide;

(R)-2-(5-((3-ethoxypyridin-2-yl)oxy)pyridin-3-yl)-N-(tetrahydrofuran-3-yl)pyrimidine-5-carboxamide; or (S)2-(5-((3-ethoxypyrazin-2-yl)oxy)pyridin-3-yl)-N-(1-hydroxy-2-methylpropan-2-yl)pyrimidine-5-carboxamide;

or a pharmaceutically acceptable salt thereof.

In another embodiment, the compound is:

(R)-2-(5-((3-ethoxypyridin-2-yl)oxy)pyridin-3-yl)-N-(3-(hydroxymethyl)tetrahydrofuran-3-yl)pyrimidine-5-carboxamide;

(S)-2-(5-((3-ethoxypyridin-2-yl)oxy)pyridin-3-yl)-N-(tetrahydrofuran-3-yl)pyrimidine-5-carboxamide; or (S)-2-(5-((3-ethoxypyridin-2-yl)oxy)pyridin-3-yl)-N-(3-(hydroxymethyl)tetrahydrofuran-3-yl)pyrimidine-5-carboxamide, or a pharmaceutically acceptable salt thereof.

In a further embodiment, the compound has the structure:

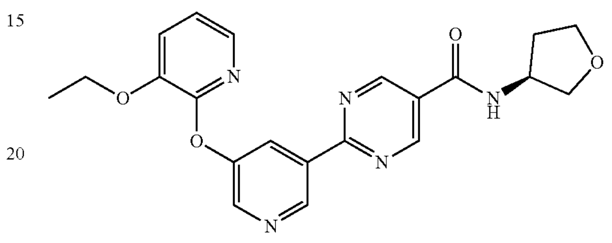

or a pharmaceutically acceptable salt thereof.

In a further embodiment, the compound of Formula (I) or (Ia) or a salt of the compound is present in a pharmaceutical composition in a therapeutically effective amount, in admixture with at least one pharmaceutically acceptable excipient.

In a further embodiment, the composition further includes at least one additional pharmaceutical agent selected from the group consisting of an anti-inflammation agent, an anti-diabetic agent, and a cholesterol/lipid modulating agent.

In an embodiment, the method for the treatment of diabetes includes the administration of an effective amount of compound of the present invention or a pharmaceutically acceptable salt of said compound to a patient in need thereof.

In another embodiment, the method for treating a metabolic or metabolic-related disease, condition or disorder includes the step of administering to a patient a therapeutically effective amount of a compound of the present invention or a pharmaceutically acceptable salt of said compound.

In another embodiment, the method for treating a condition selected from the group consisting of hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), non-alcoholic fatty liver disease (NAFLD), includes the administration of an effective amount of a compound according to the present invention or a pharmaceutically acceptable salt of said compound.

In a further embodiment, the method for treating a metabolic or metabolic-related disease, condition or disorder includes the step of administering to a patient in need of such treatment two separate pharmaceutical compositions comprising (i) a first composition according to the present invention; and (ii) a second composition comprising at least one additional pharmaceutical agent selected from the group consisting of an anti-obesity agent and an anti-diabetic agent, and at least one pharmaceutically acceptable excipient.

In yet a further embodiment, the method of the present invention is performed when said first composition and said second composition are administered simultaneously.

In yet another embodiment, the method of the present invention is performed when first composition and said second composition are administered sequentially and in any order.

In one embodiment, when two compositions are administered, the first composition and the second composition are administered simultaneously. In another embodiment, the first composition and the second composition are administered sequentially and in any order.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, WI) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie,* 4, Aufl. ed. Springer-Verlag, Berlin, including supplements (also available via the Beilstein online database)). Many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines and lower alkyl or benzyl esters for carboxylic acids) which are generally not chemically reactive under the reaction conditions described and can typically be removed without chemically altering other functionality in the Formula I and Ia compounds.

The Reaction Schemes described below are intended to provide a general description of the methodology employed in the preparation of the compounds of the present invention. Some of the compounds of the present invention contain a single chiral center. In the following Schemes, the general methods for the preparation of the compounds are shown either in racemic or enantioenriched form. It will be apparent to one skilled in the art that all of the synthetic transformations can be conducted in a precisely similar manner whether the materials are enantioenriched or racemic. Moreover the resolution to the desired optically active material may take place at any desired point in the sequence using well known methods such as described herein and in the chemistry literature.

In the Reaction Schemes I and II, the variables $D^1$, $D^2$, $R^1$, $R^2$, and $R^3$ are as described in the summary except where otherwise noted. Variable R is methyl or ethyl. Reaction Scheme I outlines general procedures that can be used to provide compounds of the present invention having Formula (I).

Reaction Scheme I
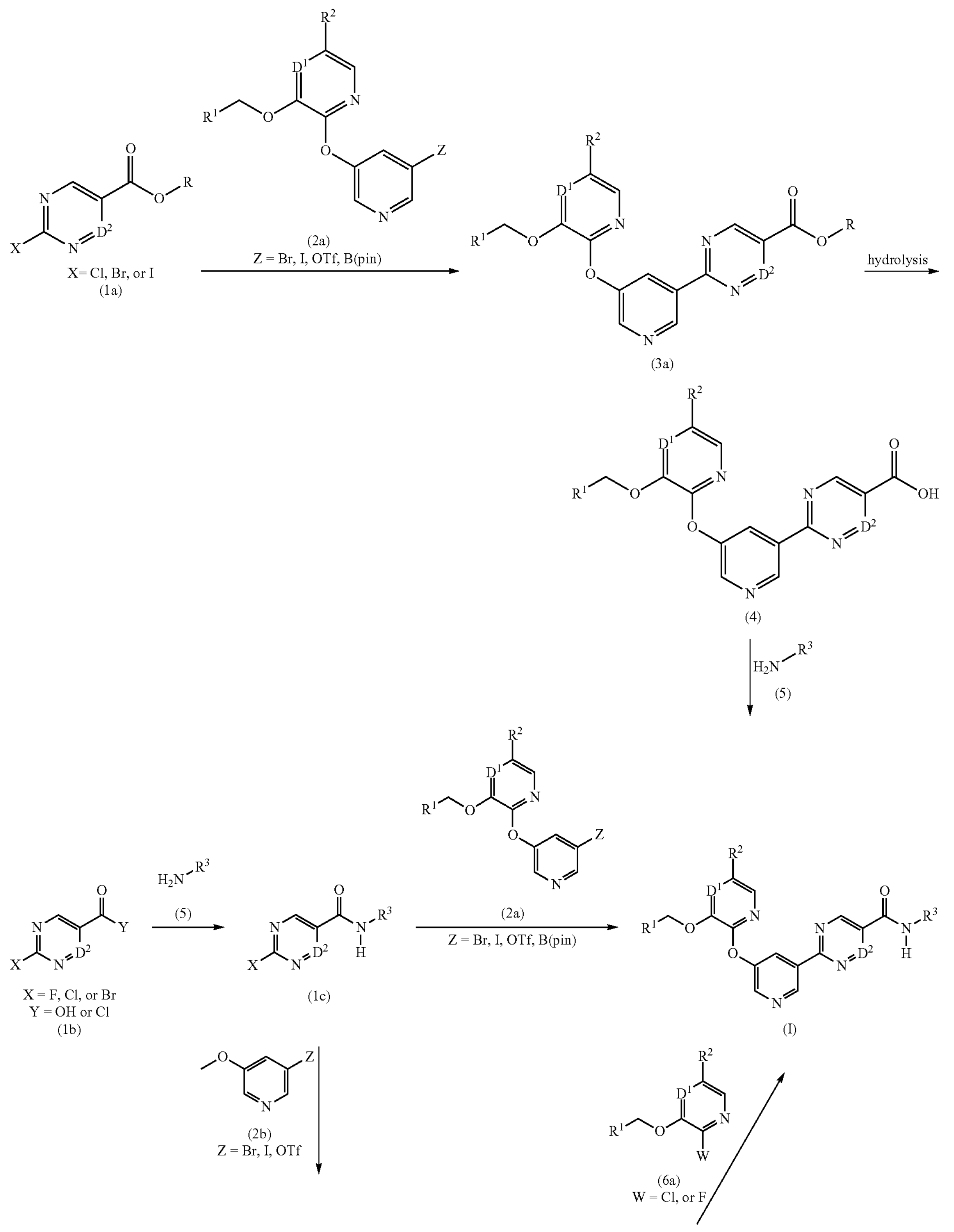

-continued

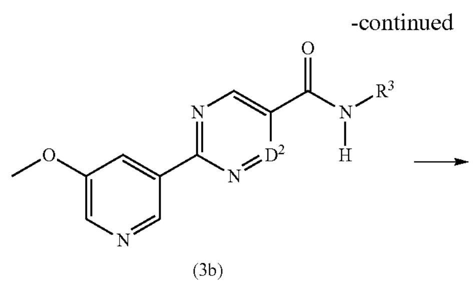

(3b)

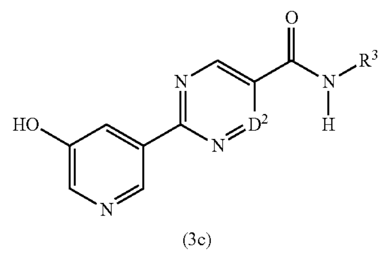

(3c)

Compounds of Formula (I) may be synthesized starting from appropriate intermediates through methods described in the literature such as: *J. Med. Chem.,* 2007, 50, 2990-3003; *Monatsh Chem,* 2012, 143, 1575-1592; *J. Med. Chem.,* 2011, 54, 6342-6363; *Org. Proc. Res. Dev.* 2014, 18, 1145-1152; *Angew. Chem. Int. Ed.* 2011, 50, 9943; *J. Am. Chem. Soc.* 2005, 127, 8146; *J. Org. Chem.* 2008, 73, 284; *Org. Lett.* 2002, 4, 973; *Org. Lett.,* 2011, 13, 1840-1843; *Metal Catalyzed Cross-Coupling Reactions and More*, Wiley-VCH, Weinheim, Germany, 2014, 3, 995; *Applications of Transition Metal Catalysis in Drug Discovery and Development*, John Wiley & Sons, Inc., Hoboken, New Jersey, USA, 2012, 3, 97. Intermediates (1a) and (1b) are commercially available and/or may be prepared via methods known to those skilled in the art. For example, intermediates (1a) and (1b) may be synthesized through methods described in the literature such as: *J. Med. Chem.* 2000, 43, 3995; *Org. Proc. Res. Dev.* 2010, 14, 936. Intermediates (2a) and (2b) are commercially available or are described in the literature and may be prepared via methods known to those skilled in the art, including those described below (Reaction Scheme II).

Intermediate (3a) may be prepared from intermediates (1a) and (2a) in a transition metal mediated coupling reaction. One of the halides (1a) or (2a) may be converted to an organometallic reagent, such as a boronic acid, zincate, stannane, or Grignard derivative using methods well known to those skilled in the art. The resulting organometallic reagent may then be reacted with the other halide intermediate in a transition metal catalyzed cross coupling reaction. Preferably, intermediate (2a) is converted to a zincate and is coupled to intermediate (1a) using a palladium or nickel catalyst in a reaction inert solvent such as toluene, 1,2-dimethoxyethane, dioxane, DMSO, DMF, or THF, in the presence of a suitable ligand, and a base such as sodium, potassium, or lithium tert-butoxide, or cesium carbonate, at a temperature between 10° C. and 130° C. by the methods described in the literature such as: *J. Med. Chem.,* 2007, 50, 2990-3003; *Monatsh Chem,* 2012, 143, 1575-1592; *J. Med. Chem.,* 2011, 54, 6342-6363; *Org. Proc. Res. Dev.* 2014, 18, 1145-1152 or other methods known to those skilled in the art.

Intermediate (4) may be prepared from ester (3a) via a hydrolysis reaction under conditions well known to those skilled in the art. Preferably, intermediate (3a, R=methyl or ethyl) is treated with an aqueous base such as sodium hydroxide, lithium hydroxide, or potassium hydroxide, in a suitable solvent or solvent mixture comprised of water, methanol, and/or THF, at a temperature between 20° C. and 60° C.

Compounds of Formula (I) may be prepared from acid (4) and amine (5) under amide forming conditions well known to those skilled in the art, using coupling reagents such as propane phosphonic acid anhydride ($T_3P$), 1,1'-carbonyldiimidazole (CDI), benzotriazo-1-yloxytris(dimethylamino) phosphonium hexafluorophosphate (BOP), 2-(1H-7-azabenzotriazol-1-yl)-1,1,3,3-tetramethyl uronium hexafluorophosphate methanaminium (HATU), oxalyl chloride, O-benzotriazol-1-yl-N,N,N',N'-tetramethyluronium hexafluoro phosphate (HBTU), 2-chloro-1,3-dimethylimidazolinium chloride (DMC), N-(3-dimethylaminopropyl)-N'-ethylcarbodiimide (EDCI) or 1-hydroxybenzotriazole (HOBT) in a reaction inert solvent such as acetonitrile, dichloromethane (DCM), DMF, DMSO, or THF in the presence of a base such as triethylamine, N-methyl-morpholine, or N,N-diisopropylethylamine at a temperature between 10° C. and 90° C., preferably between 20° C. and 65° C.

Alternatively, compounds of Formula (I) may be prepared by a two-step sequence from intermediate (1b) and amine (5) via an amide coupling reaction to afford intermediate (1c), followed by a metal mediated coupling reaction with aryl halide (2a). Preferably, intermediate (1c) is prepared from acid chloride (1b, Y=Cl) and amine (5) in the presence of a base such as triethylamine or N,N-diisopropylethylamine, in a reaction inert solvent, such as dichloromethane, at a temperature between −20° C. to 30° C., preferably between −20° C. and 0° C. Alternatively, intermediate (1c) may be prepared from acid (1b, Y=OH) and amine (5) in the presence of an amide coupling reagent, such as propane phosphonic acid anhydride ($T_3P$), 1,1'-carbonyldiimidazole (CDI), benzotriazo-1-yloxytris(dimethylamino)phosphonium hexafluorophosphate (BOP), 2-(1H-7-azabenzotriazol-1-yl)-1,1,3,3-tetramethyl uronium hexafluorophosphate methanaminium (HATU), O-benzotriazol-1-yl-N,N,N',N'-tetramethyluronium hexafluoro phosphate (HBTU), 2-chloro-1,3-dimethylimidazolinium chloride (DMC), N-(3-dimethylaminopropyl)-N'-ethylcarbodiimide (EDCI) or 1-hydroxybenzotriazole (HOBT) in a reaction inert solvent such as acetonitrile, dichloromethane, DMF, DMSO, or THF in the presence of a base such as triethylamine, N-methylmorpholine, or N,N-diisopropylethylamine at a temperature between 10° C. and 90° C. Compounds of Formula (I) may then be prepared from halides (1c) and (2a) in a transition metal mediated coupling reaction. One of the halides (1c) or (2a) may be converted to an organometallic reagent, such as a boronic acid, zincate, stannane, or Grignard derivative using methods well known to those skilled in the art. The resulting organometallic reagent may then be reacted with the other halide intermediate in a transition metal catalyzed cross coupling reaction. Preferably, intermediate (2a) is converted to a zincate and is coupled to intermediate (1c) using a palladium or nickel catalyst in a reaction inert solvent such as toluene, 1,2-dimethoxyethane, dioxane, DMSO, DMF, or THF, in the presence of a suitable ligand, and a base such as sodium, potassium, or lithium tert-butoxide, or cesium carbonate, at a temperature between 10° C. and 130° C. by the methods described in the literature such as: *J. Med. Chem.*, 2007, 50, 2990-3003; *Monatsh Chem*, 2012, 143, 1575-1592; *J. Med. Chem.*, 2011, 54, 6342-6363; *Org. Proc. Res. Dev.* 2014, 18, 1145-1152 or other methods known to those skilled in the art.

Alternatively, compounds of Formula (I) may be prepared from intermediate (1c) by a three-step sequence involving addition of heteroaryl halide (2b) followed by demethylation and addition of aryl halide (6a). Intermediate (3b) may be prepared via transition metal mediated coupling reaction starting from halides (1c) and (2b). One of the halides (1c) or (2b) may be converted to an organometallic reagent, such as boronic acid, zincate, stannane, or Grignard derivatives using methods well known to those skilled in the art. The resulting organometallic reagent may then be reacted with the other halide intermediate in a transition metal catalyzed cross coupling reaction. Preferably, intermediate (2b) is converted to a zincate and is coupled to intermediate (1c) using a palladium or nickel catalyst in a reaction inert solvent such as toluene, 1,2-dimethoxyethane, dioxane, DMSO, DMF, or THF, in the presence of a suitable ligand, and a base such as sodium, potassium, or lithium tert-butoxide, or cesium carbonate, at a temperature between 10° C. and 130° C. by the methods described in the literature such as: *J. Med. Chem.*, 2007, 50, 2990-3003; *Monatsh Chem*, 2012, 143, 1575-1592; *J. Med. Chem.*, 2011, 54, 6342-6363; *Org. Proc. Res. Dev.* 2014, 18, 1145-1152 or other methods known to those skilled in the art. Intermediate (3c) may be prepared from intermediate (3b) via demethylation using hydrohalic acids such as hydrogen bromide, bases such as sodium hydroxide or sodium alkoxide, boron tribromide, thiol or other methods known to those skilled in the art. For example, demethylation may be accomplished by methods described in the literature such as: *Arch Pharm Res* 2008, 31, 305-309; *Tetrahedron*, 2005, 61, 7833-7863; *Protecting Groups in Organic* Synthesis, John Wiley & Sons, Inc., Hoboken, New Jersey, USA, 2007, 370-382. Compounds of Formula (I) may then be prepared from heteroaryl halide (6a) in a nucleophilic aromatic substitution reaction by alcohol (3c) in a reaction inert solvent such as dimethylsulfoxide (DMSO), N,N-dimethylformamide (DMF), acetonitrile, or tetrahydrofuran (THF), in the presence of a suitable base, such as cesium carbonate, triethylamine (TEA) or N,N-diisopropylethylamine (DIPEA) at a temperature between 20° C. and 160° C. Preferably, intermediates (6a) and (3c) are reacted in DMSO, THF, or acetonitrile in the presence of triethylamine or N,N-diisopropylethylamine, at a temperature between 100° C. and 160° C. to provide compounds of Formula (I) by methods described in the literature such as: *Tetrahedron* 2005, 62 6000-6005, *Journal of Medicinal Chemistry*, 2015, 58(7), 3036-3059.

Reaction Scheme II outlines the synthesis of intermediates (2a).

Reaction Scheme II

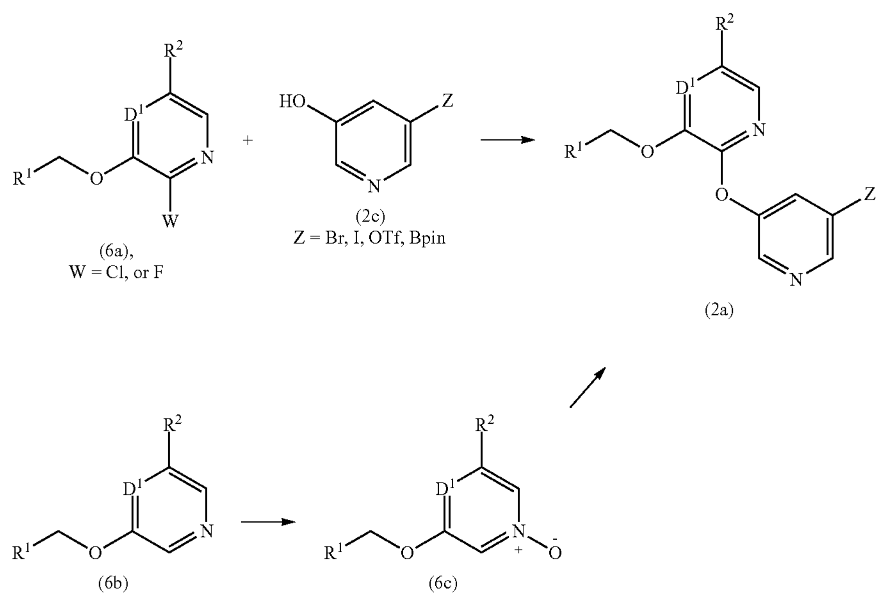

(6a), W = Cl, or F (2c) Z = Br, I, OTf, Bpin (2a)

(6b)

(6c)

Intermediates (6a), (6b), and (2c) are commercially available or are described in the literature and may be prepared via methods known to those skilled in the art. Intermediate (2a) may be synthesized via nucleophilic aromatic substitution reaction of heteroaryl halide (6a) with hydroxypyridine (2c) in a reaction inert solvent such as dimethylsulfoxide (DMSO), N,N-dimethylformamide (DMF), acetonitrile, N-methyl-2-pyrrolidinone (NMP), or tetrahydrofuran (THF), in the presence of a suitable base, such as cesium carbonate, potassium carbonate, triethylamine (TEA) or N,N-diisopropylethylamine (DIPEA) at a temperature between 20° C. and 160° C.

Preferably, intermediates (6a) and (2c) are reacted in DMSO, NMP, or acetonitrile in the presence of triethylamine or N,N-diisopropylethylamine, at a temperature between 100° C. and 160° C. to provide intermediate (2a) using methods described in the literature such as: *Tetrahedron* 2005, 62 6000-6005, *Journal of Medicinal Chemistry*, 2015, 58(7), 3036-3059. Alternatively, intermediate (2a) may be synthesized by transition metal promoted ether formation between a hydroxy-aromatic coupling partner (2c) and an aromatic halide (6a) using methods such as those described in: *Advanced Synthesis & Catalysis*, 2011, 353, 3403-3414; *Chemistry—A European Journal*, 2015, 21, 8727-8732;

Synlett 2012, 23, 101; *J. Org. Chem.* 2009, 74, 7187; *Org. Lett.* 2007, 9, 643; *Angew. Chem. Int. Ed.* 2011, 50, 9943; *J. Am. Chem. Soc.* 2005, 127, 8146; *J. Org. Chem.* 2008, 73, 284; *Org. Lett.* 2002, 4, 973. The appropriate starting materials (6a) and (2c) may be treated with a metal salt, such as copper(I) chloride, copper(I)bromide, or copper(I) iodide, and a ligand such as 2,2,6,6-tetramethylheptane-3,5-dione, 1,10-phenanthroline, or other suitable ligand, in a reaction inert solvent such as toluene, DMSO, or DMF, in the presence of a base such as potassium carbonate, cesium carbonate, or potassium phosphate, at a temperature of 80° C. to 120° C. Preferably, the appropriate starting materials (6a) and (2c) are treated with copper(I) chloride and 2,2,6,6-tetramethylheptane-3,5-dione, in toluene, in the presence cesium carbonate, at a temperature of 100° C. to 120° C.

Alternatively, intermediate (2a) may be prepared from a two-step sequence involving formation of N-oxide (6c) followed by addition of hydroxyl pyridine (2c). N-oxide (6c) may be prepared from oxidizing agents such as m-chloroperoxybenzoic acid, hydrogen peroxide, potassium permanganate, or other oxidizing agents known to those skilled in the art in a reaction inert solvent such as dichloromethane, 1,2-dichloroethane, or acetonitrile at a temperature between 0° C. and 25° C. Preferably, intermediate (6b) is reacted in dichloromethane with m-chloroperoxybenzoic acid at a temperature between 10° C. and 25° C. to provide intermediate (6c). Intermediate (2a) may be prepared from intermediate (6c) and intermediate (2c) in the presence of bromotripyrrolidinophosphonium hexafluorophosphate (PyBroP) in a reaction inert solvent such as tetrahydrofuran, dichloromethane, or dioxane at a temperature between 10° C. and 25° C. Preferably, intermediate (6c) are reacted with intermediate (2c) in the presence of bromotripyrrolidinophosphonium hexafluorophosphate in tetrahydrofuran at a temperature between 10° C. and 25° C. as described in *Org. Lett.,* 2011, 13, 1840-1843.

Combination Agents

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Thus, the methods of prevention and treatment described herein include use of combination agents.

The combination agents are administered to a mammal in a therapeutically effective amount. By "therapeutically effective amount" it is meant an amount of a compound of the present invention that, when administered alone or in combination with an additional therapeutic agent to a mammal, is effective to treat the desired disease/condition e.g., obesity, diabetes, and cardiovascular conditions such as anti-hypertensive agents and coronary heart disease.

Examples of suitable anti-diabetic agents include (e.g. insulins, metfomin, DPPIV inhibitors, GLP-1 agonists, analogues and mimetics, SGLT1 and SGLT2 inhibitors). Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., *Drug Discovery Today,* 12(9/10), 373-381 (2007)), SIRT-1 activator (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), Ertugliflozin, ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, ß3 adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, NY and Procter & Gamble Company, Cincinnati, OH), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, the combination of naltrexone with buproprion and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), the combination of naltrexone with buproprion, oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3), phentermine and topiramate (trade name: Qsymia), and sibutramine. Preferably, compounds of the present invention and combination therapies are administered in conjunction with exercise and a sensible diet.

The compounds of the present invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-COA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-COA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates; bile acid sequestrants (such as questran); ACAT inhibitors; MTP inhibitors; lipooxygenase inhibitors; choesterol absorption inhibitors; and cholesteryl ester transfer protein inhibitors. Other atherosclerotic agents include PCSK9 modulators.

In another embodiment, a compound of Formula I may be co-administered with agents for the treatment of non-alcoholic steatohepatitis (NASH) and/or non-alcoholic fatty liver disease (NAFLD), such as Orlistat, TZDs and other insulin sensitizing agents, FGF21 analogs, Metformin, Omega-3-acid ethyl esters (e.g. Lovaza), Fibrates, HMG CoA-reductase Inhibitors, Ezitimbe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 Inhibitors, Phentermine, Topiramate, Incretin (GLP and GIP) analogs and Angiotensin-receptor blockers.

In another embodiment, the additional pharmaceutical agent is selected from the group consisting of cysteamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activated receptor) activity regulators, a benzothiazepine or benzothiepine compound, an RNA antisense construct to inhibit protein tyrosine phosphatase PTPRU, a heteroatom-linked substituted piperidine and derivatives thereof, an azacyclopentane derivative capable of inhibiting stearoyl-coenzyme alpha delta-9 desaturase, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of thereof.

Additional therapeutic agents include anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, dpinephrine, nitroglycerin, nitroprusside etc.

Combination agents useful for treating vasculitis are included, for example, azathioprine, cyclophosphamide, mycophenolate, mofetil, rituximab etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the present invention include heparins (e.g., unfractioned and low molecular weight heparins such as enoxaparin and dalteparin).

In another preferred embodiment the second agent is at least one agent selected from warfarin, dabigatran, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

A preferred second agent is at least one anti-platelet agent. Especially preferred anti-platelet agents are aspirin and clopidogrel.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors P2Y1 and P2Y12, with P2Y12 being even more preferred. Preferred P2Y12 receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, dabigatran, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor Vlla inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, a Formula I compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula I may be co-administered with a loop diuretic. In still another embodiment, the loop diuretic is selected from furosemide and torsemide. In still another embodiment, one or more compounds of Formula I or Ia may be co-administered with furosemide. In still another embodiment, one or more compounds of Formula I or Ia may be co-administered with torsemide which may optionally be a controlled or modified release form of torsemide.

In another embodiment, a compound of Formula I may be co-administered with a thiazide-type diuretic. In still another embodiment, the thiazide-type diuretic is selected from the group consisting of chlorothiazide and hydrochlorothiazide. In still another embodiment, one or more compounds of Formula I or Ia may be co-administered with chlorothiazide. In still another embodiment, one or more compounds of Formula I or Ia may be co-administered with hydrochlorothiazide.

In another embodiment, one or more compounds of Formula I or Ia may be co-administered with a phthalimidine-type diuretic. In still another embodiment, the phthalimidine-type diuretic is chlorthalidone. Examples of suitable mineralocorticoid receptor antagonists include sprionolactone and eplerenone. Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

The dosage of the additional pharmaceutical agent is generally dependent upon a number of factors including the health of the subject being treated, the extent of treatment desired, the nature and kind of concurrent therapy, if any, and the frequency of treatment and the nature of the effect desired. In general, the dosage range of the additional pharmaceutical agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of treatment of the invention, a compound of the present invention or a combination of a compound of the present invention and at least one additional pharmaceutical agent (referred to herein as a "combination") is administered to a subject in need of such treatment, preferably in the form of a pharmaceutical composition. In the combination aspect of the invention, the compound of the present invention and at least one other pharmaceutical agent (e.g., another anti-obesity agent) may be administered either separately or in a pharmaceutical composition comprising both. It is generally preferred that such administration be oral.

When a combination of a compound of the present invention and at least one other pharmaceutical agent are administered together, such administration may be sequential in time or simultaneous. Simultaneous administration of drug combinations is generally preferred. For sequential administration, a compound of the present invention and the additional pharmaceutical agent may be administered in any order. It is generally preferred that such administration be oral. It is especially preferred that such administration be oral and simultaneous. When a compound of the present invention and the additional pharmaceutical agent are administered sequentially, the administration of each may be by the same or by different methods.

According to the methods of the invention, a compound of the present invention or a combination is preferably administered in the form of a pharmaceutical composition. Accordingly, a compound of the present invention or a combination can be administered to a patient separately or together in any conventional oral, rectal, transdermal, parenteral (e.g., intravenous, intramuscular or subcutaneous), intracisternal, intravaginal, intraperitoneal, topical (e.g., powder, ointment, cream, spray or lotion), buccal or nasal dosage form (e.g., spray, drops or inhalant).

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20. sup.th ed. 2000.

Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerine or propylene glycol (e.g., Miglyol®

812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multi-particulate preparations (granules). In such solid dosage forms, a compound of the present invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel. TM. from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-sol™), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i) one or more lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-sol™, Explotab™, starch and sodium lauryl sulphate.

When present a disintegrant will usually comprise less than 10% of the formulation or less than 5%, for example about 3%. A preferred lubricant is magnesium stearate. When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyole® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Capmul™ MCM (medium chain mono- and diglycerides, fromAbitec), Migyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about C.sub.8 to C.sub.10) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the present invention or combinations include ointments, creams, lotions, powders and sprays. The drugs are admixed with a pharmaceutically acceptable excipient, diluent or carrier, and any preservatives, buffers, or propellants that may be required.

Many of the present compounds are poorly soluble in water, e.g., less than about 1. mu.g/mL. Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. Patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/ml of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(R0-102) (15.8%), sodium starch (7%), sodium lauryl sulfate (2%) and magnesium stearate (1%).

The HPMCAS polymers are available in low, medium and high grades as Aqoa.sup.(R)-LF, Aqoat.sup.(R)-MF and Aqoat.sup.(R)-HF respectively from Shin-Etsu Chemical Co., LTD, Tokyo, Japan. The higher MF and HF grades are generally preferred.

The following paragraphs describe exemplary formulations, dosages, etc. useful for non-human animals. The administration of the compounds of the present invention and combinations of the compounds of the present invention with anti-obesity agents can be effected orally or non-orally.

An amount of a compound of the present invention or combination of a compound of the present invention with another anti-obesity agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about 10. sub.-3 to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

Paste Formulations may be prepared by dispersing the drug in a pharmaceutically acceptable oil such as peanut oil, sesame oil, corn oil or the like.

Pellets containing an effective amount of a compound of the present invention, pharmaceutical composition, or combination may be prepared by admixing a compound of the present invention or combination with a diluent such as carbowax, carnuba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

EXAMPLES

Unless specified otherwise, starting materials are generally available from commercial sources such as Aldrich Chemicals Co. (Milwaukee, WI), Lancaster Synthesis, Inc. (Windham, NH), Acros Organics (Fairlawn, NJ), Maybridge Chemical Company, Ltd. (Cornwall, England) and Tyger Scientific (Princeton, NJ). Certain common abbreviations and acronyms have been employed which may include: AcOH (acetic acid), DBU (1,8-diazabicyclo[5.4.0]undec-7-ene), CDI (1,1'-carbonyldiimidazole), DCM (dichloromethane), DEA (diethylamine), DIPEA (N,N-diisopropylethylamine), DMAP (4-dimethylaminopyridine), DMF (N,N'-dimethylformamide), DMSO (dimethylsulfoxide), EDCI (N-(3-dimethylaminopropyl)-N'-ethylcarbodiimide), $Et_2O$ (diethyl ether), EtOAc (ethyl acetate), EtOH (ethanol), HATU (2-(1H-7-azabenzotriazol-1-yl)-1,1,3,3-tetramethyl uronium hexafluorophosphate methanaminium), HBTU (O-benzotriazol-1-yl-N,N,N',N'-tetramethyluronium hexafluoro phosphate), HOBT (1-hydroxybenzotriazole), IPA (isopropyl alcohol), KHMDS (potassium hexamethyldisilazane), MeOH (methanol), MTBE (tert-butyl methyl ether), NaBH(OAc)3 (sodium triacetoxyborohydride), NaHMDS (sodium hexamethyldisilazane), NMP (N-methylpyrrolidone), SEM ([2-(Trimethylsilyl)ethoxy]methyl), TEA (triethylamine), TFA (trifluoroacetic acid), THF (tetrahydrofuran), and $T_3P$ (propane phosphonic acid anhydride).

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wisconsin or DriSolv™ products from EMD Chemicals, Gibbstown, NJ) were employed. Commercial solvents and reagents were used without further purification. When indicated, reactions were heated by microwave irradiation using Biotage Initiator or Personal Chemistry Emrys Optimizer microwaves. Reaction progress was monitored using thin layer chromatography (TLC), liquid chromatography-mass spectrometry (LCMS), high performance liquid chromatography (HPLC), and/or gas chromatography-mass spectrometry (GCMS) analyses. TLC was performed on pre-coated silica gel plates with a fluorescence indicator (254 nm excitation wavelength) and visualized under UV light and/or with 12, $KMnO_4$, $CoCl_2$, phosphomolybdic acid, and/or ceric ammonium molybdate stains. LCMS data were acquired on an Agilent 1100 Series instrument with a Leap Technologies autosampler, Gemini C18 columns, MeCN/water gradients, and either TFA, formic acid, or ammonium hydroxide modifiers. The column eluent was analyzed using Waters ZQ mass spectrometer scanning in both positive and negative ion modes from 100 to 1200 Da. Other similar instruments were also used. HPLC data were acquired on an Agilent 1100 Series instrument using Gemini or XBridge C18 columns, MeCN/water gradients, and either TFA or ammonium hydroxide modifiers. GCMS data were acquired using a Hewlett Packard 6890 oven with an HP 6890 injector, HP-1 column (12 m×0.2 mm×0.33 μm), and helium carrier gas. The sample was analyzed on an HP 5973 mass selective detector scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were performed by chiral supercritical fluid chromatography (SFC) using Berger or Thar instruments; ChiralPAK-AD, -AS, -IC, Chiralcel-OD, or -OJ columns; and $CO_2$ mixtures with MeOH, EtOH, iPrOH, or MeCN, alone or modified using TFA or $iPrNH_2$. UV detection was used to trigger fraction collection.

Mass spectrometry data are reported from LCMS analyses. Mass spectrometry (MS) was performed via atmospheric pressure chemical ionization (APCI), electrospray Ionization (ESI), electron impact ionization (EI) or electron scatter (ES) ionization sources. Proton nuclear magnetic spectroscopy ($^1H$ NMR) chemical shifts are given in parts per million downfield from tetramethylsilane and were recorded on 300, 400, 500, or 600 MHz Varian spectrometers. Chemical shifts are expressed in parts per million (ppm, δ) referenced to the deuterated solvent residual peaks. The peak shapes are described as follows: s, singlet; d, doublet; t, triplet; q, quartet; quin, quintet; m, multiplet; br s, broad singlet; app, apparent. Analytical SFC data were acquired on a Berger analytical instrument as described above. Optical rotation data were acquired on a PerkinElmer model 343 polarimeter using a 1 dm cell. Silica gel chromatography was performed primarily using a medium pressure Biotage or ISCO systems using columns pre-packaged by various commercial vendors including Biotage and ISCO. Microanalyses were performed by Quantitative Technologies Inc. and were within 0.4% of the calculated values.

Unless otherwise noted, chemical reactions were performed at room temperature (about 23 degrees Celsius).

The compounds and intermediates described below were named using the naming convention provided with ChemBioDraw Ultra, Version 12.0 (CambridgeSoft Corp., Cambridge, Massachusetts). The naming convention provided with ChemBioDraw Ultra, Version 12.0 are well known by those skilled in the art and it is believed that the naming convention provided with ChemBioDraw Ultra, Version 12.0 generally comports with the IUPAC (International Union for Pure and Applied Chemistry) recommendations on Nomenclature of Organic Chemistry and the CAS Index rules. Unless noted otherwise, all reactants were obtained commercially without further purifications or were prepared using methods known in the literature.

The terms "concentrated", "evaporated", and "concentrated in vacuo" refer to the removal of solvent at reduced pressure on a rotary evaporator with a bath temperature less than 60° C. The abbreviation "min" and "h" stand for "minutes" and "hours" respectively. The term "TLC" refers to thin layer chromatography, "room temperature or ambient temperature" means a temperature between 18 to 25° C., "GCMS" refers to gas chromatography-mass spectrometry, "LCMS" refers to liquid chromatography-mass spectrometry, "UPLC" refers to ultra performance liquid chromatography and "HPLC" refers to high pressure liquid chromatography, "SFC" refers to supercritical fluid chromatography.

Hydrogenation may be performed in a Parr Shaker under pressurized hydrogen gas, or in Thales-nano H-Cube flow hydrogenation apparatus at full hydrogen and a flow rate between 1-2 mL/min at specified temperature.

HPLC, UPLC, LCMS, GCMS, and SFC retention times were measured using the methods noted in the procedures.

Preparation of Intermediates and Examples

General Procedure A: Add diisopropylethylamine (3.0 equiv) to a solution of Intermediate 1 or Intermediate 2 (1 equiv) in dimethylformamide or tetrahydrofuran (0.15 M). HATU (1.0 equiv) and the appropriate amine (2.0 equiv) were added sequentially to a vial. The reaction mixture was stirred at room temperature for 16 h. The reaction was concentrated and purified by preparative HPLC to afford the specified product unless otherwise noted.

General Procedure B: Add oxalyl chloride (2.0 eq, 2M in dichloromethane) to a suspension of Intermediate 1 or Intermediate 2 (1.0 equiv) in dichloromethane (0.1M). Dimethylformamide (10 uL) was added to the suspension and the reaction mixture was stirred at room temperature for 30 minutes. The suspension turned to a solution over this time. The appropriate amine (1.0 equiv) and diisopropylethylamine (2.3 equiv) in dichloromethane (0.5 mL) was added to the reaction mixture and stirred at room temperature for 16 hours. The reaction was diluted with dichloromethane (2 mL) and washed sequentially with 1N sodium hydroxide (100 uL) and brine (100 uL). The organic layer was dried over magnesium sulfate, filtered, and the solvent was evaporated under reduced pressure. The resulting residue was purified by preparative HPLC to afford the specified product unless otherwise noted.

Intermediate 1: 2-(5-((3-ethoxypyridin-2-yl)oxy) pyridin-3-yl)pyrimidine-5-carboxylic Acid

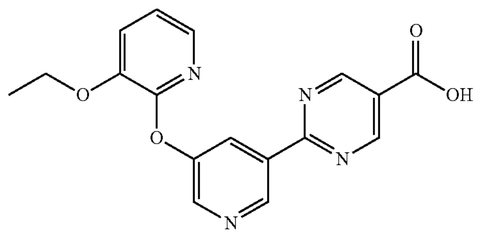 [SMILES: CCOc1cccnc1Oc1cncc(-c2ncc(C(=O)O)cn2)c1]

Step 1: 3-Ethoxypyridine

Cesium carbonate (12 mol, 1.5 equiv) and ethyl iodide (9.7 mol, 1.2 equiv) were added to a solution of 3-hydroxypyrdine (8.10 mol, 1.0 equiv) in acetone (12 L) at 15° C. The reaction mixture was stirred at room temperature for 24 hours. The reaction mixture was filtered and the organic layer was concentrated to give crude product. Ethyl acetate (20 L) was added and washed with water (3×5 L). The organic layer was dried over sodium sulfate, filtered and concentrated to give 3-ethoxypyridine (620 g, 62%) as an oil. $^1$H NMR (400 MHZ, $CDCl_3$) δ1.44 (t, 3H), 4.07 (q, 2H), 7.15-7.23 (m, 2H), 8.20 (dd, 1H), 8.30 (d, 1H).

Step 2: 3-Ethoxypyridine-1-oxide m-Chloroperoxybenzoic acid (6.5 mol, 1.3 equiv) was added to a solution of 3-ethoxypyridine (5.0 mol, 1.0 equiv) in dichloromethane (12 L) at 10° C. The reaction mixture was stirred at room temperature for 24 hours. Sodium thiosulfate (4 kg, in 5 L of water) was added. The reaction mixture was stirred at 15° C. for 2 hours. Another portion of sodium thiosulfate (1.5 kg, in 5 L of water) was added. The reaction mixture was stirred at 15° C. for 1 hour. The mixture was extracted with dichloromethane (16×10 L). The combined organic layers were concentrated to give crude product. The crude product was purified by silica gel column chromatography (dichloromethane:methanol; 100:1-10:1) to give the title compound (680 g, 97%) as brown oil. This was further purified by trituration with petroleum ether (4 L) at room temperature for 24 hours to give 3-ethoxypyridine-1-oxide (580 g, 83%) as yellow solid. $^1$H NMR (400 MHZ, $CDCl_3$) δ1.41 (t, 3H), 4.02 (q, 2H), 6.84 (dd, 1H), 7.12 (dd, 1H), 7.85 (d, 1H), 7.91-7.95 (m, 1H).

Step 3: 2-((5-Bromopyridin-3-yl)oxy)-3-ethoxypyridine

This reaction was carried out in five parallel batches.

Diisopropylethylamine (2.69 mol, 3.7 equiv) and bromotripyrrolidinophosphonium hexafluorophosphate (0.93 mol, 1.3 equiv) were added to a stirred solution of 3-ethoxypyridine-1-oxide (0.72 mol, 1.0 equiv) and 3-bromo-5-hydroxypyridine (0.72 mol, 1.0 equiv) in tetrahydrofuran (2500 mL) at room temperature. The reaction mixture was stirred at room temperature for 2 days then the separate batches were combined to a single batch. The resulting suspension was concentrated to dryness and dissolved in dichloromethane (25 L). The organic layer was washed with 1N sodium hydroxide (15 L), water (3×20 L), and brine (20 L). The organic layer was dried over sodium sulfate, filtered and concentrated to give an oil. The crude oil was purified by silica gel column chromatography (petroleum ether: ethyl acetate; 10:1-1:1) to give crude product as brown solid. This solid was triturated with methyl tert-butyl ether: petroleum ether (1:10; 11 L) to afford 2-((5-bromopyridin-3-yl)oxy)-3-ethoxypyridine (730 g, 69%) as off yellow solid. $^1$H NMR (400 MHZ, $CDCl_3$) δ1.49 (t, 3H), 4.16 (q, 2H), 7.04 (dd, 1H), 7.25 (dd, 1H), 7.68-7.73 (m, 2H), 8.44 (d, 1H), 8.49 (d, 1H). MS (ES+) 297.1 (M+H).

Step 4: Ethyl 2-(5-((3-ethoxypyridin-2-yl)oxy)pyridin-3-yl)pyrimidine-5-carboxylate A solution of 2-((5-bromopyridin-3-yl)oxy)-3-ethoxypyridine (300 mmol, 1.0 equiv) in tetrahydrofuran (1.3 L) was degassed with nitrogen for 30 minutes. Turbo Grignard (390 mmol, 1.3 equiv, 1.3 M in tetrahydrofuran) was added at room temperature at a rate to maintain the internal temperature below 30° C. The reaction mixture was allowed to cool to room temperature and stirred for 3 hours. The reaction was cooled to 10° C. and zinc chloride (390 mmol, 1.3 equiv, 1.9 M in 2-methyltetrahydrofuran) was added at a rate to maintain the temperature below 15° C. The resulting suspension was warmed to room temperature until all the precipitate was dissolved and then cooled back to 10° C. Ethyl 2-chloropyrimidine-5-carboxylate (360 mmol, 1.2 equiv) and dichloro[bis(2-(diphenylphosphino)phenyl) ether]palladium(II) (6.00 mmol, 0.02 equiv) were added as solids. The resulting suspension was degassed with nitrogen for 30 minutes then heated to 50° C. for 16 hours. The reaction was worked up under aqueous conditions then treated sequentially with ethylenediaminetetraacetic acid disodium salt, thiosilica, and charcoal to remove metal impurities. The crude compound was recrystallized from methanol (450 mL) to yield ethyl 2-(5-((3-ethoxypyridin-2-yl)oxy)pyridin-3-yl)pyrimidine-5-carboxylate (77 g, 70%) as a pale, yellow solid. $^1$H NMR (400 MHZ, $CDCl_3$) δ1.44 (t, 3H), 1.50 (t, 3H), 4.19 (q, 2H), 4.46 (q, 2H), 7.00-7.04 (m, 1H), 7.25 (s, 1H), 7.71 (d, 1H), 8.59 (s, 1H), 8.66 (d, 1H), 9.32 (s, 2H), 9.55 (s, 1H).

Step 5: 2-(5-((3-ethoxypyridin-2-yl)oxy)pyridin-3-yl)pyrimidine-5-carboxylic Acid Sodium hydroxide (307 mmol, 1.5 equiv, 4M aqueous) and methanol (50 mL) were added to a suspension of 2-(5-((3-ethoxypyridin-2-yl)oxy)pyridin-3-yl)pyrimidine-5-carboxylate (205 mmol, 1.0 equiv) in tetrahydrofuran (300 mL). The resulting solution was stirred at room temperature for 3 hours. The reaction mixture was diluted with water (400 mL) and extracted with 2:1 diethyl ether:heptanes (2×300 mL). The aqueous layer was acidified to pH of 4 with 4M hydrochloric acid. The resulting suspension was stirred at room temperature for 1 hour. The solid was filtered, washed with water, and dried to yield 2-(5-((3-ethoxypyridin-2-yl)oxy)pyridin-3-yl)pyrimidine-5-carboxylic acid (69 g, 100%) as a pale, yellow solid. $^1$H NMR (400 MHZ, DMSO-$d_6$) δ1.37 (t, 3H), 4.18 (q, 2H), 7.19 (dd, 1H), 7.58 (dd, 1H), 7.70 (dd, 1H), 8.35-8.40 (m, 1H), 8.66 (d, 1H), 9.33 (s, 2H), 9.41 (d, 1H), 13.9 (br. s, 1H).

Intermediate 2: 3-{5-[(3-Ethoxypyridin-2-yl)oxy]pyridin-3-yl}-1,2,4-triazine-6-carboxylic Acid

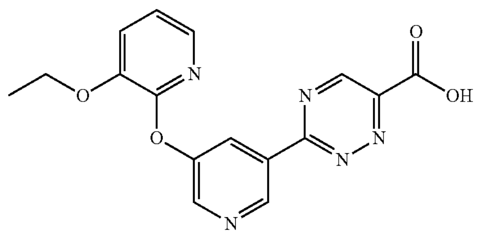 [SMILES: CCOc1cccnc1Oc1cncc(-c2ncc(C(=O)O)nn2)c1]

Step 1. 6-Bromo-1,2,4-triazin-3-amine

Water (120 mL) was added to a mixture of 3-amino-1,2,4-triazine (104 mmol, 1.0 equiv) in acetonitrile (120 mL) and stirred at room temperature until a brown solution was formed. The mixture was cooled to 0° C., treated with N-bromosuccinimide (109 mmol, 1.05 equiv) in a portion-wise manner and stirred at 0° C. for 20 min. After warming to room temperature, the mixture was diluted with ethyl acetate (350 mL) and cooled to 0° C. Sodium carbonate (12 g) was added to the mixture and stirred for 10 min. The two layers were separated and the aqueous phase was extracted with ethyl acetate (200 mL). The combined organic layers were washed with aqueous sodium bicarbonate, dried over sodium sulfate, filtered and concentrated to give the 6-bromo-1,2,4-triazin-3-amine (10.5 g, 58%) as a yellow solid. $^1$H NMR (400 MHZ, $CD_3OD$) 8.32 (s, 1H).

Step 2. Ethyl 3-amino-1,2,4-triazine-6-carboxylate

In two separate batches, palladium acetate (0.87 mmol, 0.05 equiv) was added to a solution of 6-bromo-1,2,4-triazin-3-amine (17 mmol, 1.0 equiv), triethylamine (35 mmol, 2.0 equiv) and xantphos (1.40 mmol, 0.08 equiv) in ethanol (60 mL) was added. The mixture was degassed with carbon monoxide and stirred at 85° C. under an atmosphere of carbon monoxide (16 Psi) for 16 h. The cooled reaction mixture was diluted with ethyl acetate (60 mL), filtered through a pad of celite and concentrated. The crude products from both batches were combined and purified using column chromatography (ethyl acetate/petroleum ether=3:7) to give ethyl 3-amino-1,2,4-triazine-6-carboxylate (2.5 g, 88%) as a yellow solid. $^1$H NMR (400 MHZ, $CDCl_3$) δ1.49 (t, 3H), 4.50 (q, 2H), 8.79 (s, 1H).

Step 3. ethyl 3-chloro-1,2,4-triazine-6-carboxylate tert-Butyl nitrite (4.5 mmol, 1.5 equiv) was added to a solution of ethyl 3-amino-1,2,4-triazine-6-carboxylate (3.0 mmol, 1.0 equiv) and copper(II) chloride (3.6 mmol, 1.2 equiv) in acetonitrile (15 mL) in a dropwise manner. The resulting mixture was heated at 60° C. for 1 h. The reaction mixture was cooled to room temperature and treated with cold hydrochloric acid (10 mL, 1N). The mixture was extracted with ethyl acetate (3×30 mL) and the combined organic layers were dried over sodium sulfate, filtered and evaporated. The crude product was purified using column chromatography eluting with ethyl acetate/petroleum ether (5:95 to 1:1) to give ethyl 3-chloro-1,2,4-triazine-6-carboxylate (300 mg, 54%) as a yellow solid. $^1$H NMR (400 MHZ, $CDCl_3$) δ1.50 (t, 3H), 4.58 (q, 2H), 9.11 (s, 1H).

Step 4. 3-Ethoxy-2-{[5-(tributylstannanyl)pyridin-3-yl]oxy}pyridine

Tetrakis(triphenylphosphine)palladium(0) (0.68 mmol, 0.10 equiv) was added to a solution of 2-[(5-bromopyridin-3-yl)oxy]-3-ethoxypyridine (6.8 mmol, 1.0 equiv) and hexabutyldistannane (7.5 mmol, 1.1 equiv) in dioxane (40 mL) under an atmosphere of nitrogen. The reaction was heated to 110° C. and stirred at this temperature for 16 h. The mixture was quenched with aqueous potassium fluoride and stirred for 1 h. The resulting suspension was filtered through a pad of celite and the filtrate was extracted with ethyl acetate (3×60 mL). The combined organics were washed with brine, dried over sodium sulfate, filtered and concentrated. The crude product was purified using column chromatography (ethyl acetate/petroleum ether=0:100 to 1:4) to give 3-ethoxy-2-{[5-(tributylstannanyl)pyridin-3-yl]oxy}pyridine (1.6 g, 47%) as a yellow oil. $^1$H NMR (400 MHZ, $CDCl_3$) δ0.88 (t, 9H), 1.06-1.11 (m, 6H), 1.32 (s, 6H), 1.47-1.58 (m, 9H), 4.17 (q, 2H), 6.99 (dd, 1H), 7.22 (dd, 1H), 7.57 (dd, 1H), 7.70 (dd, 1H), 8.37-8.40 (m, 2H).

Step 5. Ethyl 3-{5-[(3-ethoxypyridin-2-yl)oxy]pyridin-3-yl}-1,2,4-triazine-6-carboxylate Tetrakis(triphenylphosphine)palladium(0) (0.05 mmol, 0.05 equiv) was added to a mixture of 3-ethoxy-2-{[5-(tributylstannanyl)pyridin-3-yl]oxy}pyridine (0.99 mmol, 1.0 equiv) and ethyl 3-chloro-1,2,4-triazine-6-carboxylate (0.99 mmol, 1.0 equiv) in dioxane (8 mL). The vial was degassed to remove oxygen by bubbling through nitrogen gas gently for 2 min. The vial was then stirred at 115° C. for 30 min under microwave irradiation. The reaction mixture was cooled to room temperature, treated with aqueous potassium fluoride, and stirred for 1 h. The suspension was filtered through a pad of celite and the filtrate was extracted with ethyl acetate (3×30 mL). The combined organic layers were washed with brine, dried over sodium sulfate and concentrated. The crude material was purified using column chromatography (ethyl acetate/petroleum ether=1:4 to 1:1) to give ethyl 3-{5-[(3-ethoxypyridin-2-yl)oxy]pyridin-3-yl}-1,2,4-triazine-6-carboxylate (150 mg, 41%) as a yellow oil. MS (ES+) 368.0 (M+H).

Step 6. 3-{5-[(3-ethoxypyridin-2-yl)oxy]pyridin-3-yl}-1,2,4-triazine-6-carboxylic Acid Sodium hydroxide (1.0 mmol, 20 equiv, 2M) was added to a solution of ethyl 3-{5-[(3-ethoxypyridin-2-yl)oxy]pyridin-3-yl}-1,2,4-triazine-6-carboxylate (0.053 mmol, 1.0 equiv) in methanol (1 mL) at room temperature. The solution was stirred for 1 h. The mixture was concentrated to remove methanol, diluted with water, and extracted with dichloromethane (2×15 mL). The aqueous layer was acidified to pH=5 with 2 N hydrochloric acid and extracted with ethyl acetate (3×10 mL). The combined organic layers were washed with brine (20 mL), dried over anhydrous sodium sulfate, filtered and concentrated to dryness to give the product (15 mg, 83%) as a light yellow solid. MS (ES+) 339.9 (M+H).

Intermediate 3: 2-{5-[(3-ethoxypyrazin-2-yl)oxy]pyridin-3-yl}pyrimidine-5-carboxylic Acid

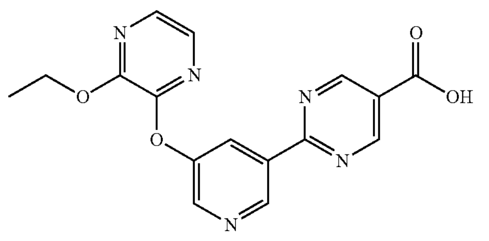 [SMILES: CCOc1nccnc1Oc1cncc(-c2ncc(C(=O)O)cn2)c1]

Step 1. 2-[(5-bromopyridin-3-yl)oxy]-3-ethoxypyrazine

5-Bromopyridin-3-ol (32 mmol, 1.0 equiv) and cesium carbonate (39 mmol, 1.3 equiv) were added to a solution of 2-chloro-3-ethoxypyrazine (32 mmol, 1.0 equiv) in N-methyl-2-pyrrolidone (250 mL). The reaction mixture was stirred at 150° C. for 1 h. The cooled reaction mixture was poured into water (300 mL) and extracted with ethyl acetate (3×250 mL). The combined organic layers were dried over sodium sulfate, filtered and concentrated. The crude product was purified using column chromatography eluting with petroleum ether/ethyl acetate (0% to 100%) to give the title compound (5.0 g, 54%) as a white solid. $^1$H NMR (400 MHZ, $CDCl_3$) δ1.50 (t, 3H), 4.54 (q, 2H), 7.59 (d, 1H), 7.77 (t, 1H), 7.83 (d, 1H), 8.49 (d, 1H), 8.56 (d, 1H).

Step 2. Ethyl 2-{5-[(3-ethoxypyrazin-2-yl)oxy]pyridin-3-yl}pyrimidine-5-carboxylate

[1,1'-Bis(diphenylphosphino) ferrocene] dichloropalladium (II) complex with dichloromethane (124 mg, 0.05 eq) was added to a suspension of 2-((5-bromopyridin-3-yl)oxy)-3-ethoxypyrazine (3.4 mmol, 1.0 equiv), bis(pinacolato) diboron (4.1 mmol, 1.2 eq), and potassium acetate (13 mmol, 4.0 eq) in dioxane (5 mL). The reaction mixture was purged with nitrogen and stirred at 100° C. for 2 hours. The reaction was cooled to room temperature and quenched with water (50 mL). The mixture was extracted with ethyl acetate (25 mL) and washed with brine (3×50 mL). The organic layer was concentrated to provide 2-ethoxy-3-((5-(4,4,5,5-tetramethyl-1,3,2-dioxaborolan-2-yl)pyridin-3-yl)oxy)pyrazine (1.4 g, 110%) as a black oil that was used directly in the next step.

Ethyl-2-chloropyrimidine-5-carboxylate (930 mg, 1.2 eq), potassium carbonate (1.1 g, 2.0 equiv), and [1,1'-bis (diphenylphosphino) ferrocene] dichloropalladium (II) complex with dichloromethane (150 mg, 0.05 eq) were added to a solution of 2-ethoxy-3-((5-(4,4,5,5-tetramethyl-1,3,2-dioxaborolan-2-yl)pyridin-3-yl)oxy)pyrazine (1.4 g, 4.1 mmol) in dioxane (5 mL). The black suspension was flushed with nitrogen and stirred at 80° C. for 16 hours. The reaction was cooled to room temperature and quenched with water (50 mL). The mixture was extracted with ethyl acetate (25 mL), washed with brine (3×50 mL) and dried to black residue. The crude was purified by flash chromatography (ethyl acetate in petroleum ether) to afford ethyl 2-{5-[(3-ethoxypyrazin-2-yl)oxy]pyridin-3-yl}pyrimidine-5-carboxylate (700 mg, 46%) as a yellow solid. MS (ES+) 367.9 (M+H).

Step 4. 2-{5-[(3-ethoxypyrazin-2-yl)oxy]pyridin-3-yl}pyrimidine-5-carboxylic Acid Sodium hydroxide (6.8 mmol, 5.0 equiv, 2M) was added to ethyl 2-{5-[(3-ethoxypyrazin-2-yl)oxy]pyridin-3-yl}pyrimidine-5-carboxylate (1.4 mmol, 1.0 equiv) in ethanol (5 mL). The reaction was stirred at 30° C. for 16 hours. Methyl-tert-butyl ether (30 mL) was added to the reaction mixture and the resulting solid was filtered and dried to provide 2-{5-[(3-ethoxypyrazin-2-yl)oxy]pyridin-3-yl}pyrimidine-5-carboxylic acid (500 mg, 101%) as the sodium salt. $^1$H NMR (300 MHZ, DMSO-$d_6$) δ1.42 (t, 3H), 4.48 (q, 2H), 7.67 (s, 1H), 7.93 (s, 1H), 8.54 (s, 1H), 8.74 (s, 1H), 9.33 (s, 2H), 9.45 (s, 1H).

Intermediate 4: 2-(5-((3-(2-Fluoroethoxy)pyridin-2-yl)oxy)pyridin-3-yl)pyrimidine-5-carboxylic Acid

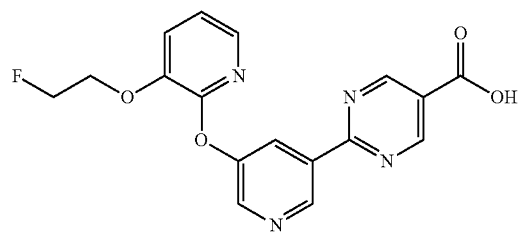 [SMILES: O=C(O)c1cnc(-c2cncc(Oc3ncccc3OCCF)c2)nc1]

Step 1: 3-(2-Fluoroethoxy)pyridine

Potassium carbonate (1.5 g, 2.0 equiv) was added to a solution of 3-hydroxypyridine (500 mg, 1 equiv) and 1-fluoro-2-iodoethane (920 mg, 1.0 equiv) in dimethylformamide (10 mL). The suspension was stirred at 30° C. for 16 hours. The reaction was diluted with 10% methanol in dichloromethane (90 mL) and washed with water (20 mL). The organic layer was washed with brine, dried over sodium sulfate and concentrated. The crude material was purified by flash chromatography (gradient: 0-4.5% methanol in dichloromethane) to afford 3-(2-fluoroethoxy)pyridine (500 mg, 67%) as a brown oil. $^1$H NMR (400 MHZ, $CDCl_3$) δ4.19-4.33 (m, 2H), 4.67-4.74 (m, 1H), 4.79-4.86 (m, 1H), 7.22 (dd, 2H), 8.24 (t, 1H), 8.34 (t, 1H).

Step 2: 3-(2-Fluoroethoxy)pyridine 1-oxide m-Chloroperoxybenzoic acid (2.49 g, 1.2 equiv) was added to a solution of 3-(2-fluoroethoxy)pyridine (1.7 g, 1.0 equiv) in dichloromethane (30 mL). The reaction was stirred at room temperature for 16 hours. The reaction was purified directly by flash chromatography (gradient: 0-5% methanol in dichloromethane) to yield 3-(2-fluoroethoxy)pyridine 1-oxide (1.2 g, 63%) as a white solid. $^1$H NMR (400 MHZ, $CDCl_3$) δ4.16-4.22 (m, 1H), 4.23-4.29 (m, 1H), 4.66-4.73 (m, 1H), 4.77-4.84 (m, 1H), 6.90 (dd, 1H), 7.17 (dd, 1H), 7.87-7.94 (m, 1H), 7.99 (t, 1H).

Step 3: 2-((5-Bromopyridin-3-yl)oxy)-3-(2-fluoroethoxy)pyridine

Diisopropylethylamine (5.2 mL, 3.8 equiv) was added to a solution of 3-(2-fluoroethoxy)pyridine 1-oxide (1.2 g, 1.0 equiv), 3-bromo-5-hydroxypyridine (1.3 g, 1.0 equiv) and bromotripyrrolidinophosphonium hexafluorophosphate (4.6 g, 1.3 equiv) in tetrahydrofuran (25 mL) at 13° C. The mixture was stirred at room temperature for 16 hours. The reaction was quenched with water (20 mL) and extracted with ethyl acetate (50 mL). The combined organics were washed with saturated ammonium chloride (3×20 mL) and brine (100 mL), dried over sodium sulfate, and concentrated. The crude material was purified by flash chromatography (gradient: 0-70% ethyl acetate in petroleum ether) to provide 2-((5-Bromopyridin-3-yl)oxy)-3-(2-fluoroethoxy)pyridine (1.9 g, 81%) as a yellow oil. $^1$H NMR (400 MHZ, $CDCl_3$) δ4.28-4.33 (m, 1H), 4.34-4.41 (m, 2H), 4.70-4.78 (m, 1H), 4.82-4.82 (m, 1H), 7.05 (dd, 1H), 7.31 (dt, 1H), 7.69-7.73 (m, 1H), 7.74-7.80 (m, 2H), 8.44 (dd, 1H), 8.48-8.52 (m, 2H).

Step 4: 2-(5-((3-(2-Fluoroethoxy)pyridin-2-yl)oxy) pyridin-3-yl)pyrimidine-5-carboxylic Acid Bis(pinacolato)diboron (580 mg, 1.2 equiv), potassium acetate (560 mg, 3.0 equiv), and [1,1'-Bis(diphenylphosphino) ferrocene] dichloropalladium (II) complex with dichloromethane (70 mg, 0.05 equiv) was added to a solution of 2-((5-Bromopyridin-3-yl)oxy)-3-(2-fluoroethoxy) pyridine (600 mg, 1.0 equiv) in dioxane (10 mL) at room temperature. The reaction was stirred at 100° C. for 16 hours. The reaction mixture was diluted with ethyl acetate (60 mL), washed with water (20 mL) and brine, then concentrated to a residue. The residue was diluted with dioxane (15 mL) and water (5 mL). Ethyl 2-chloropyrimidine-5-carboxylate (310 mg, 1.0 equiv), [1,1'-Bis(diphenylphosphino) ferrocene] dichloropalladium (II) complex with dichloromethane (61 mg, 0.05 equiv), and potassium carbonate (460 mg, 2.0 equiv) were added to the reaction mixture and the resulting suspension was stirred at 80° C. for 16 hours. The suspension was filtered and then partitioned between ethyl acetate (30 mL) and water (50 mL). The aqueous layer was extracted with ethyl acetate (2×30 mL). The combined organic layers were washed with brine (50 mL), dried over sodium sulfate, filtered, and concentrated to provide crude material that was purified by prep-TLC (5% methanol in dichloromethane) to afford 2-(5-((3-(2-fluoroethoxy)pyridin-2-yl)oxy)pyridin-3-yl)pyrimidine-5-carboxylic acid (80 mg, 13%). MS (ES+) 357.0 (M+H).

Example 1: (S)-2-(5-((3-ethoxypyridin-2-yl)oxy) pyridin-3-yl)-N-(tetrahydrofuran-3-yl)pyrimidine-5-carboxamide

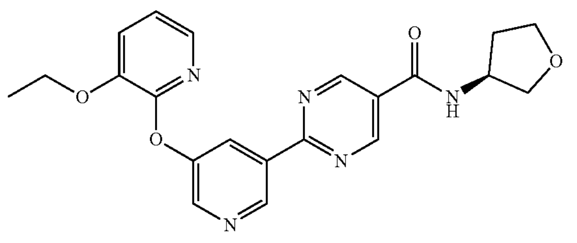 [SMILES: CCOc1cccnc1Oc1cncc(-c2ncc(C(=O)N[C@H]3CCOC3)cn2)c1]

Oxalyl chloride (13.8 mL, 160 mmol, 1.2 equiv) and dimethylformamide (0.510 mL, 6.65 mmol, 0.05 equiv) were added to a suspension of 2-(5-((3-ethoxypyridin-2-yl) oxy)pyridin-3-yl)pyrimidine-5-carboxylic acid (45.0 g, 133 mmol, 1.0 equiv) in dichloromethane (500 mL). The suspension was stirred for 2 hours when a solution was achieved. The reaction mixture was concentrated to yield crude acid chloride as a red solid. A solution of (S)-tetrahydrofuran-3-amine (12.2 g, 140 mmol, 1.05 equiv) and diisopropylethylamine (51.0 mL, 293 mmol, 2.2 equiv) in tetrahydrofuran (100 mL) was added dropwise to a solution of the crude acid chloride in dichloromethane (200 mL) at 0° C. The reaction was allowed to warm to room temperature and stirred for 16 hours. Water (1.0 L) and ethyl acetate (600 mL) were added and the organic layer was separated, washed with saturated sodium bicarbonate, dried over magnesium sulfate, and filtered. The filtrate was treated with activated charcoal (20 g) was stirred at 65° C. for 20 minutes. The suspension was filtered warm and filtrate was concentrated to a pale, yellow solid which was recrystallized from methanol in ethyl acetate (1:4, 1 L) to yield (S)-2-(5-((3-ethoxypyridin-2-yl)oxy)pyridin-3-yl)-N-(tetrahydrofuran-3-yl)pyrimidine- 5-carboxamide (43.5 g, 81%) as a colorless solid. The title compound was combined with previous batches (108.7 g, 266.8 mmol) prepared in the same manner and slurried with ethyl acetate (1.0 L) at 80° C. for 4 hours. The suspension was allowed to cool to room temperature and stirred for 4 days. The solid was filtered, washed with ethyl acetate (3×200 mL) and dried under high vacuum at 50° C. for 24 hours to yield (S)-2-(5-((3-ethoxypyridin-2-yl)oxy)pyridin-3-yl)-N-(tetrahydrofuran-3-yl)pyrimidine-5-carboxamide (100.5 g, 92%) as a colorless solid. $^1$H NMR (300 MHZ, DMSO-$d_6$) δ1.38 (t, 3H), 1.89-1.98 (m, 1H), 2.15-2.26 (m, 1H), 3.65 (dd, 1H), 3.70-3.78 (m, 1H), 3.85-3.92 (m, 2H), 4.18 (q, 2H), 4.46-4.55 (m, 1H), 7.18 (dd, 1H), 7.58 (dd, 1H), 7.69 (dd, 1H), 8.37 (dd, 1H), 8.64 (d, 1H), 8.95 (d, 1H), 9.28 (s, 2H), 9.39 (d, 1H). MS (ES+) 408.4 (M+H). Melting point 177.5° C. Elemental analysis for $C_{21}H_{21}N_5O_4$: calculated C, 61.91; H, 5.20; N, 17.19; found C, 61.86; H, 5.18; N, 17.30.

The solid form from this procedure was characterized by Powder X-ray diffraction (PXRD) analysis and assigned as Form 1.

Alternative preparation for (S)-2-(5-((3-ethoxypyridin-2-yl)oxy)pyridin-3-yl)-N-(tetrahydrofuran-3-yl) pyrimidine-5-carboxamide (Example 1)

A 100 mL reactor was charged with acetonitrile (35 mL), 2-(5-((3-ethoxypyridin-2-yl)oxy)pyridin-3-yl)pyrimidine-5-carboxylic acid (5.0 g, 15 mmol) and (S)-tetrahydrofuran-3-amine hydrochloride (2.2 g, 18 mmol, 1.2 equiv).

Diisopropylethylamine (18 mL, 103 mmol, 7.0 equiv) was charged while maintaining the temperature at 20° C. to 30° C. A solution of propane phosphonic acid anhydride (T3P) in acetonitrile (21 mL, 30 mmol, 2.0 equiv) was charged at a rate that maintained the temperature below 45° C. The reactor was heated to 40±5° C. for 1 hour then sampled for reaction completion. The reaction was cooled to 20° C. to 25° C. and tetrahydrofuran (25 mL) was added. A solution of sodium bicarbonate (0.5M, 40 mL) was charged and the mixture was stirred for 1 hour. The pH was checked and measured at 8.5. Ethyl acetate (40 mL) was added and the mixture stirred for 15 minutes. The mixture was settled and the phases split. The aqueous layer was transferred to a separatory funnel and back extracted with ethyl acetate (100 mL). The organic phases were combined and washed with water (40 mL). The organic layer was transferred to a 100 mL reactor in portions and concentrated under vacuum to a low volume. Methyl ethyl ketone (100 mL) was added and the mixture was concentrated to a final volume of approximately 60 mL. Vacuum was removed and the slurry was heated to reflux and held until the solids were washed down the reactor walls. The slurry was cooled to 15° C. over 2 hours and granulated overnight. The solids were isolated by filtration, washing the reactor and cake twice with methyl ethyl ketone (10 mL each). The solids were dried in a vacuum oven at 50° C. to yield 4.86 g (81%) of the desired product. The solid form from this procedure was characterized by PXRD analysis and assigned as Form 2.

Conversion of the Form 2 to the Form 1

To a 100 mL reactor was charged Form 2 of (S)-2-(5-((3-ethoxypyridin-2-yl)oxy)pyridin-3-yl)-N-(tetrahydrofuran-3-yl)pyrimidine-5-carboxamide (Example 1) (10.0 g, 24.6 mmol, 1.00 equiv.), Methyl ethyl ketone (8.8 mL/g), 88.0 mL) and water (1.2 mL/g, 12.0 mL). The reactor was heated to 50° C. over 30 minutes. A complete solution appeared at approximately 44° C. The reactor was cooled to 40° C. over 30 minutes then seed Form 1 of (S)-2-(5-((3-ethoxypyridin-2-yl)oxy)pyridin-3-yl)-N-(tetrahydrofuran-3-yl)pyrimidine-5-carboxamide (Example 1) (0.050 g, 0.123 mmol, 0.0050 equiv.) was charged. After seeding, the hazy slurry was stirred for 1 hour before cooling to 5° C. over 2 hours and then stirred at 5° C. for 12 hours. An in process control sample was pulled and characterized by PXRD analysis to confirm the solids were Form 1. The slurry was filtered, and the reactor and cake was washed with 0° C. methyl ethyl ketone (2.5 mL/g, 25 mL). The solids were dried in a vacuum oven at 50° C. to yield 8.15 g (81.5%) of the desired product. PXRD patterns of the desired product were consistent with Form 1.

Powder X-Ray Diffraction

Powder X-ray diffraction analysis was conducted using a Bruker AXS D8 Advance diffractometer equipped with a Cu radiation source (Kα-average wavelength of 1. 54056 Å), equipped with a twin primary utilizing a gobel mirror. Diffracted radiation was detected by a PSD-Lynx Eye detector. Both primary and secondary equipped with 2.5 soller slits. The X-ray tube voltage and amperage were set at 40 kV and 40 mA respectively. Data was collected in the Theta-Theta goniometer in a locked couple scan from 3.0 to 40.0 degrees 2-Theta with 1000 steps using a scan speed of 6 seconds per step. Samples were prepared by placement in a silicon low background sample holder (C79298A3244B261). Data were collected using Bruker DIFFRAC Plus software. Analysis performed by EVA diffract plus software.

The PXRD data file was not processed prior to peak searching. Using the peak search algorithm in the EVA software, peaks were selected with a threshold value of 5 and a width value of 0.2. The output of automated assignments was visually checked to ensure validity and adjustments manually made if necessary. Peaks with relative intensity of ≥3% were generally chosen. The peaks which were not resolved or were consistent with noise were also discarded. A typical error associated with the peak position from PXRD stated in USP is within +/−0.2° (USP-941).

TABLE 1

| Key PXRD peaks to characterize crystalline material of Example 1 | |
|---|---|
| Form 1 of Example 1 | Form 2 of Example 1 |
| Angle 2Θ (°) 5.3, 7.7, 15.4 | Angle 2Θ (°) 6.5, 9.3, 13.6 |

FIG. 1 is a characteristic x-ray powder diffraction pattern showing crystalline form 1 of Example 1 (Vertical Axis: Intensity (CPS); Horizontal Axis: Two theta (degrees)).

Figure 2:
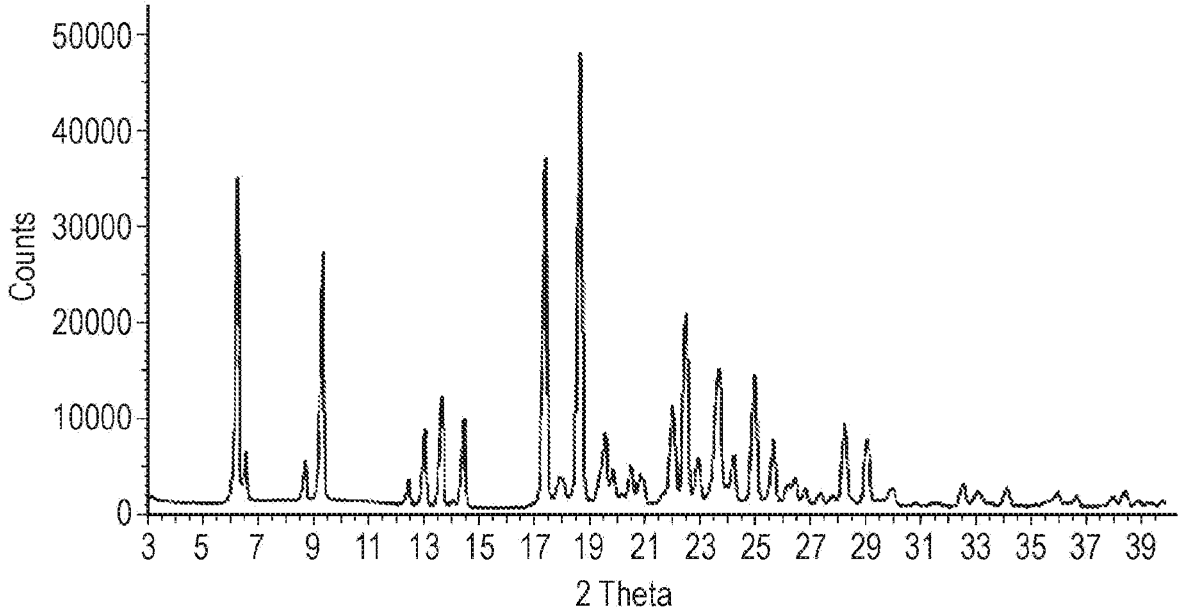
FIG. 2 is a characteristic x-ray powder diffraction pattern showing crystalline Form 2 of Example 1 (Vertical Axis: Intensity (CPS); Horizontal Axis: Two theta (degrees)).

FIG. 2 is a characteristic x-ray powder diffraction pattern showing crystalline form 2 of Example 1 (Vertical Axis: Intensity (CPS); Horizontal Axis: Two theta (degrees)).

Example 2: (R)-2-(5-((3-Ethoxypyridin-2-yl)oxy)pyridin-3-yl)-N-(tetrahydrofuran-3-yl)pyrimidine-5-carboxamide

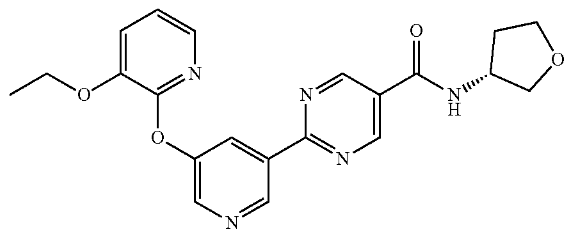 [SMILES: CCOc1cccnc1Oc1cncc(-c2ncc(C(=O)N[C@@H]3CCOC3)cn2)c1]

The title compound was prepared using general method A with Intermediate 1 (0.31 mmol, 1.0 equiv) and (R)-(+)-tetrahydro-3-furylamine toluenesulfonate salt (124 mg, 1.5 eq). The crude product was purified by flash chromatography using ethyl acetate in heptanes to yield (R)-2-(5-((3-ethoxypyridin-2-yl)oxy)pyridin-3-yl)-N-(tetrahydrofuran-3-yl)pyrimidine-5-carboxamide (91 mg, 70%). $^1$H NMR (400 MHZ, DMSO-$d_6$) δ1.38 (t, 3H), 1.89-1.98 (m, 1H), 2.15-2.28 (m, 1H), 3.5 (dd, 1H), 3.70-3.78 (m, 1H), 3.85-3.92 (m, 2H), 4.19 (q, 2H), 4.46-4.55 (m, 1H), 7.19 (dd, 1H), 7.58 (dd, 1H), 7.69 (dd, 1H), 8.37 (dd, 1H), 8.64 (d, 1H), 8.96 (d, 1H), 9.28 (s, 2H), 9.39 (d, 1H). MS (ES+) 408.3 (M+H).

Examples 3.1-3.7: The Examples in Table 2 were prepared by the general procedure A using the appropriate starting materials and analyzed by the methods described below. The $R^3$ variable, intermediates (which varies $R^1$, $D^1$, and/or $D^2$) used, and analysis method is noted in Table 2.

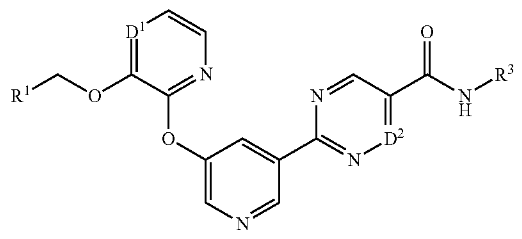

Analytical Methods

Method A: Xbridge C18, 2.1×50 mm, 5 μm, 40° C., Mobile Phase A 0.0375% TFA in water, Mobile Phase B 0.01875% TFA in acetonitrile, Gradient: 0.00 min 1% B, 0.60 min 5% B, 4.00 min 100% B, 0.8 mL/min, API-ES+.

Method B: Xbridge C18, 2.1×50 mm, 5 μm, 40° C., Mobile Phase A 0.05% $NH_4OH$ in water, Mobile phase B 100% acetonitrile, Gradient 0.00 min 5% B, 3.40 min 100% B, 0.8 mL/min, API-ES+.

Method C: Waters Atlantis dC18 4.6×50, 5 um, Mobile phase A: 0.05% TFA in water (v/v); Mobile phase B: 0.05% TFA in acetonitrile (v/v), Gradient: 95.0% $H_2O$/5.0% Acetonitrile linear to 5% $H_2O$/95% Acetonitrile in 4.0 min, HOLD at 5% $H_2O$/95% Acetonitrile to 5.0 min. Flow: 2 mL/min Method D: Waters XBridge C18 4.6×50, 5 um, Mobile phase A: 0.03% $NH_4OH$ in water (v/v); Mobile phase B: 0.03% $NH_4OH$ in acetonitrile (v/v), Gradient: 95.0% $H_2O$/5.0% Acetonitrile linear to 5% $H_2O$/95% Acetonitrile in 4.0 min, HOLD at 5% $H_2O$/95% Acetonitrile to 5.0 min. Flow: 2 mL/min.

Method E: Xtimate C18 5×30 mm, 3 um

Mobile phase A: 0.1% TFA in water, Mobile Phase B: acetonitrile, Gradient: 0.00 min 1% B, 1 min 5% B, 5 min 100% B, 8 min 1% B. Flow rate: 1.2 mL/min Method F: LCMS E(4-302) XBridge C18 2.1*50 mm, 5 um Mobile phase: 1.0% acetonitrile in water (0.1% formic acid) to 5% acetonitrile in water (0.1% formic acid) in 0.6 min; then from 5.0% acetonitrile in water (0.1% formic acid) to 100% acetonitrile (0.1% formic acid) in 3.4 minutes; then back to 1.0% acetonitrile in water (0.1% formic acid) till 4.3 min, and hold 0.7 minutes. Flow rate: 0.8 ml/min Method G: Xbridge C18, 2.0×50 mm, 5 μm, 40° C., Mobile Phase A 10 mM $NH_4HCO_3$ in water, Mobile phase B 100% acetonitrile, Gradient 1.0% B to 5% B in 0.6 min, 100% B in 3.4 minutes; then back to 1.0% B within 0.3 min. Flow rate: 0.8 ml/min

TABLE 2

| Example | Compound Name | $R^3$ | Intermediate Number | MS (ES+) (M + H) | Retention Time (min) and analytical method |
|---|---|---|---|---|---|
| 3.1 | 2-(5-((3-ethoxypyridin-2-yl)oxy)pyridin-3-yl)-N-(3-methyl-1,1-dioxidotetrahydrothiophen-3-yl)pyrimidine-5-carboxamide | 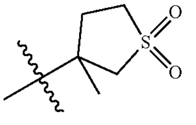 [SMILES: *C1(C)CCS(=O)(=O)C1] | 1 | 470 | 2.310 Method C |
| 3.2 | N-(1,3-dihydroxy-2-methylpropan-2-yl)-2-(5-((3-ethoxypyridin-2-yl)oxy)pyridin-3-yl)pyrimidine-5-carboxamide | 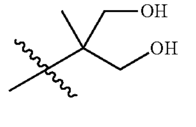 [SMILES: *C(C)(CO)CO] | 1 | 426 | 1.683 Method D |
| 3.3 | N-(1,1-dioxido-tetrahydro-thiophen-3-yl)-2-(5-((3-ethoxypyridin-2-yl)oxy)pyridin-3-yl)pyrimidine-5-carboxamide | 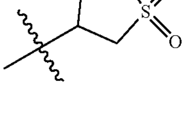 | 1 | 456 | 3.319 Method E |
| 3.4 | (S)-3-(5-((3-ethoxypyridin-2-yl)oxy)pyridin-3-yl)-N-(tetrahydrofuran-3-yl)-1,2,4-triazine-6-carboxamide | 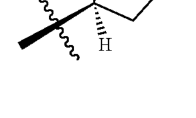 | 2 | 409 | 2.517 Method F |
| 3.5 | 2-(5-((3-ethoxypyrazin-2-yl)oxy)pyridin-3-yl)-N-(1-hydroxy-2-methylpropan-2-yl)pyrimidine-5-carboxamide | 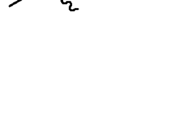 | 3 | 411 | 2.274 Method C |
| 3.6 | 2-(5-((3-ethoxypyridin-2-yl)oxy)pyridin-3-yl)-N-(2-methyl-1-(methylsulfonyl)propan-2-yl)pyrimidine-5-carboxamide | 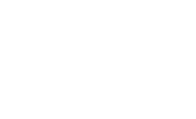 | 1 | 472 | 2.548 Method F |
| 3.7 | (S)-2-(5-((3-(2-fluoroethoxy)pyridin-2-yl)oxy)pyridin-3-yl)-N-(tetrahydrofuran-3-yl)pyrimidine-5-carboxamide | 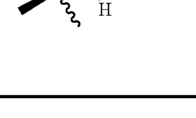 | 4 | 425.9 | 2.325 Method F |

Example 4: N-(2-cyanopropan-2-yl)-2-(5-((3-ethoxypyridin-2-yl)oxy)pyridin-3-yl)pyrimidine-5-carboxamide

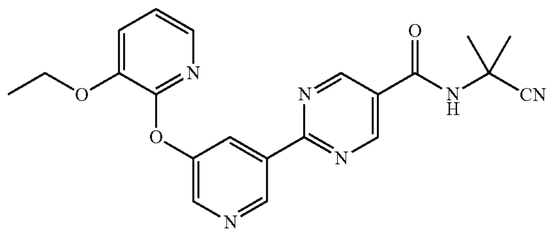 [SMILES: CCOc1cccnc1Oc1cncc(-c2ncc(C(=O)NC(C)(C)C#N)cn2)c1]

The title compound was prepared following general procedure B with Intermediate 1 (1.0 g, 1.0 equiv) and 2-amino-2-methylpropionitrile (436 mg, 1.1 eq). The crude product was purified by flash chromatography (50-100% ethyl acetate in heptanes) and treated with charcoal. The resulting residue was recrystallized from ethyl acetate (8 mL) to yield N-(2-cyanopropan-2-yl)-2-(5-((3-ethoxypyridin-2-yl)oxy)pyridin-3-yl)pyrimidine-5-carboxamide (1.1 g, 92%) as a colorless solid. $^1H$ NMR (400 MHZ, DMSO-$d_6$) δ1.38 (t, 3H), 1.74 (s, 6H), 4.18 (q, 2H), 7.18 (dd, 1H), 7.57 (dd, 1H), 7.69 (dd, 1H), 8.38 (dd, 1H), 8.66 (d, 1H), 9.18 (br. s, 1H), 9.30 (s, 2H), 9.40 (d, 1H). MS (ES+) 405.3 (M+H).

Example 5: 2-(5-((3-Ethoxypyridin-2-yl)oxy)pyridin-3-yl)-N-(1-hydroxy-2-methylpropan-2-yl)pyrimidine-5-carboxamide

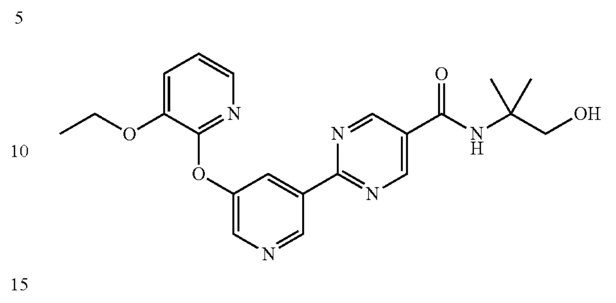

The title compound was prepared following general procedure A with Intermediate 1 (260 mg, 1.0 equiv) and 2-amino-2-methylpropan-1-ol (103 mg, 1.5 eq). The crude product was purified by flash chromatography (50-100% ethyl acetate in heptanes) and recrystallized from ethyl acetate: methanol to yield 2-(5-((3-Ethoxypyridin-2-yl)oxy)pyridin-3-yl)-N-(1-hydroxy-2-methylpropan-2-yl)pyrimidine-5-carboxamide (236 mg, 75%) as a colorless solid. $^1H$ NMR (400 MHZ, DMSO-$d_6$) δ1.33 (s, 6H), 1.38 (t, 3H), 3.55 (d, 2H), 4.18 (q, 2H), 4.83 (t, 1H), 7.18 (dd, Hz, 1H), 7.58 (d, 1H), 7.70 (d, 1H), 8.04 (br. s, 1H), 8.34-8.37 (m, 1H), 8.64 (d, 1H), 9.22 (s, 2H), 9.39 (d, 1H). MS (ES+) 410.3 (M+H).

Table 3 includes the hepatic clearance profile (Clint, app in HLM) of Example 5, which showed significant improvement when compared with Example 19.21 in WO2015140658. This significantly reduced clearance is much greater than would have been predicted given the difference in the structures and DGAT2 IC50 values of Example 5 and Example 19.21 of WO2015140658.

TABLE 3

DGAT2 Potency and Metabolic Clearance in HLM

| Example No. | Structure | DGAT2 $IC_{50}$ [nM] | $Cl_{int, app}$ in HLM [μL/min/mg] |
|---|---|---|---|
| Example 5 | 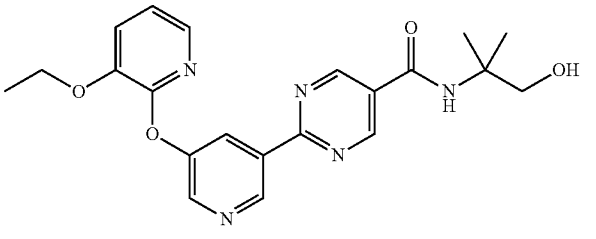 [SMILES: CCOc1cccnc1Oc1cncc(-c2ncc(C(=O)NC(C)(C)CO)cn2)c1] | 14 | 18 |
| WO2015140658 Example 19.21 | 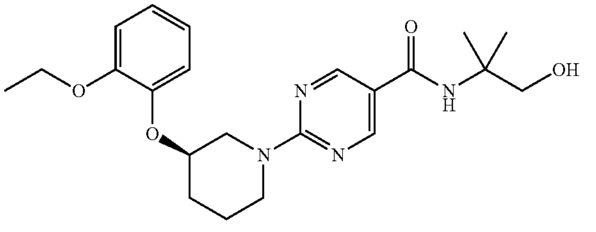 [SMILES: CCOc1ccccc1O[C@@H]1CCCN(c2ncc(C(=O)NC(C)(C)CO)cn2)C1] | 7.9 | 121 |

Examples 6a and 6b: (R)-2-(5-((3-ethoxypyridin-2-yl)oxy)pyridin-3-yl)-N-(3-(hydroxymethyl)tetrahydrofuran-3-yl)pyrimidine-5-carboxamide and (S)-2-(5-((3-ethoxypyridin-2-yl)oxy)pyridin-3-yl)-N-(3-(hydroxymethyl)tetrahydrofuran-3-yl)pyrimidine-5-carboxamide

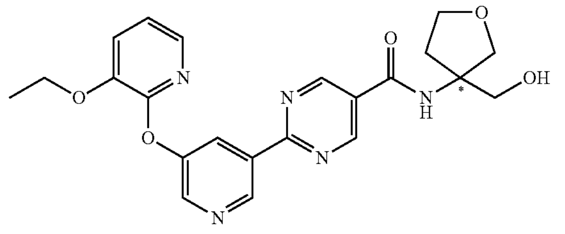 [SMILES: CCOc1cccnc1Oc1cncc(-c2ncc(C(=O)NC3(CO)CCOC3)cn2)c1]

The title compounds were prepared using general procedure A with Intermediate 1 (840 mg, 1 equiv) and (3-aminotetrahydrofuran-3-yl)methanol (320 mg, 1.1 eq). The crude product was passed through a plug of silica to yield the racemate as a yellow solid which was separated by chiral SFC purification: Chiral Tech AD-H 250 mm×4.6 mm 5 u; Isocratic 70% A: carbon dioxide; Mobile phase in 30% B: 0.2% isopropylamine in isopropanol (v/v). Flow: 60 mL/min; back pressure=120 Bar. The first peak to elute off the column is Example 6a, and the second peak is Example 6b.

Enantiomer 1: SFC retention time=9.31 minutes. (330 mg) This compound was further purified by column chromatography (methanol in dichloromethane) then recrystallized from methanol in ethyl acetate to afford enantiomer 6a (218 mg, 20%) as a colorless solid. $^1H$ NMR (400 MHZ, $CD_3OD$) δ1.40 (t, 3H), 2.23 (dt, 1H), 2.29-2.37 (m, 1H), 3.82-3.91 (m, 2H), 3.92-3.95 (m, 2H), 3.96-4.04 (m, 2H), 4.17 (q, 2H), 7.19 (dd, 1H), 7.52 (dd, 1H), 7.71 (dd, 1H), 8.49 (dd, 1H), 8.52 (d, 1H), 9.22 (s, 2H), 9.41 (d, 1H). MS (ES+) 438.3 (M+H).

Enantiomer 2: SFC retention time =9.59 minutes (300 mg). This compound was further purified by column chromatography (methanol in dichloromethane) then recrystallized from methanol in ethyl acetate to afford enantiomer 6b (205 mg, 19%) as a colorless solid. $^1H$ NMR (400 MHZ, $CD_3OD$) δ1.40 (t, 3H), 2.23 (dt, 1H), 2.29-2.37 (m, 1H), 3.82-3.91 (m, 2H), 3.92-3.95 (m, 2H), 3.96-4.04 (m, 2H), 4.17 (q, 2H), 7.19 (dd, 1H), 7.52 (dd, 1H), 7.71 (dd, 1H), 8.49 (dd, 1H), 8.52 (d, 1H), 9.22 (s, 2H), 9.41 (d, 1H).MS (ES+) 438.3 (M+H).

Example 7: 3-{5-[(3-ethoxypyridin-2-yl)oxy]pyridin-3-yl}-N-(1-hydroxy-2-methylpropan-2-yl)-1,2,4-triazine-6-carboxamide

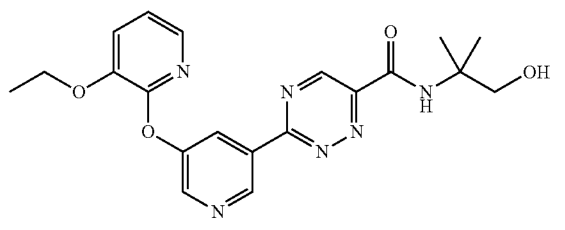 [SMILES: CCOc1cccnc1Oc1cncc(-c2ncc(C(=O)NC(C)(C)CO)nn2)c1]

The title compound was prepared according to general procedure A using Intermediate 2 (15 mg, 0.04 mmol) and 2-amino-2-methyl-1-propanol (4.73 mg, 0.053 mmol). The crude product was purified by reverse-phase preparatory HPLC to give the title compound (2.8 mg, 16%) as a light yellow solid. $^1H$ NMR (400 MHZ, $CD_3OD$) δ1.40 (t, 3H), 1.47 (s, 6H), 3.70 (s, 2H), 4.16 (q, 2H), 7.20 (dd, 1H), 7.53 (dd, 1H), 7.71 (dd, 1H), 8.56-8.58 (m, 1H), 8.61 (d, 1H), 9.32 (s, 1H), 9.48 (d, 1H). MS (ES+) 411.0 (M+H).

Example 8: (S)-2-(5-((3-Ethoxy-5-fluoropyridin-2-yl)oxy)pyridin-3-yl)-N-(tetrahydrofuran-3-yl)pyrimidine-5-carboxamide

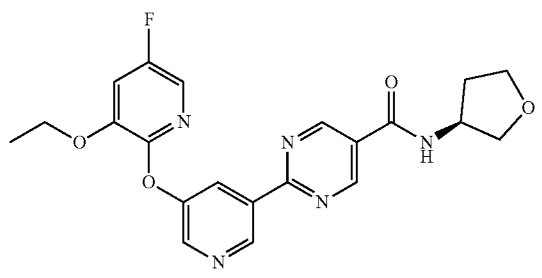 [SMILES: CCOc1cc(F)cnc1Oc1cncc(-c2ncc(C(=O)N[C@H]3CCOC3)cn2)c1]

Step 1: 3-Ethoxy-5-fluoropyridine-1-oxide

Cesium carbonate (21.6 g, 3.0 equiv) was added to a solution of 5-fluoro-3-pyridinol (25 g, 1.0 equiv) and ethyl iodide (3.8 g, 1.1 equiv). The reaction was stirred at room temperature for 16 hours. The mixture was filtered and concentrated to afford 3-ethoxy-5-fluoropyridine (3.1 g, 100%) as a yellow oil which was used without further purification. m-Chloroperoxybenzoic acid (5.7 g, 1.5 equiv) was added to a solution of 3-ethoxy-5-fluoropyridine (3.1 g, 1.0 equiv) in dichloromethane (50 mL). The reaction was stirred at room temperature for 16 hours. The reaction was purified directly by flash chromatography (gradient: 0-5% methanol in dichloromethane) to yield 3-ethoxy-5-fluoropyridine-1-oxide (3.30 g, 95%) as a white solid. $^1H$ NMR (400 MHZ, $CD_3OD$) δ1.40 (t, 3H), 4.14 (q, 2H), 7.20 (dt, 1H), 7.96-7.98 (m, 1H), 8.04-8.08 (m, 1H).

Step 2: 2-((5-Bromopyridin-3-yl)oxy)-3-ethoxy-5-fluoropyridine

Diisopropylethylamine (3.08 g, 3.8 equiv) was added to a solution of 3-ethoxy-5-fluoropyridine-1-oxide (1.0 g, 1.0 equiv) and bromotripyrrolidinophosphonium hexafluorophosphate (3.86 g, 1.3 equiv) in tetrahydrofuran (60 mL) at 0° C. The mixture was stirred at room temperature for 16 hours. The reaction was quenched with water (150 mL) and extracted with ethyl acetate (3×50 mL). The combined organics were washed with brine (100 mL), dried over sodium sulfate, and concentrated. The crude material was purified by flash chromatography (gradient: 4-24% ethyl acetate in petroleum ether) to provide 2-((5-bromopyridin-3-yl)oxy)-3-ethoxy-5-fluoropyridine (200 mg, 10%) as a white solid. $^1H$ NMR (400 MHZ, $CDCl_3$) δ1.48 (t, 3H), 4.12 (q, 2H), 7.04 (dd, 1H), 7.56-7.59 (m, 1H), 7.66-7.67 (m, 1H), 8.41-8.42 (m, 1H), 8.48-8.50 (m, 1H).

Step 3: Ethyl 2-(5-((3-ethoxy-5-fluoropyridin-2-yl)oxy)pyridin-3-yl)pyrimidine-5-carboxylate Bis(pinacolato)diboron (243 mg, 1.2 equiv), potassium acetate (235 mg, 3.0 equiv), and [1,1'-Bis(diphenylphosphino) ferrocene] dichloropalladium (II) complex with dichloromethane (29 mg, 0.05 equiv) was added to a solution of 2-((5-bromopyridin-3-yl)oxy)-3-ethoxy-5-fluoropyridine (250 mg, 1.0 equiv) in dioxane (5 mL) at room temperature. The reaction was stirred at 100° C. for 2 hours and then cooled to room temperature. The reaction mixture was diluted with ethyl acetate (60 mL) and filtered through celite. The filtrate was concentrated to a residue then diluted with dioxane (5 mL) and water (1 mL). Ethyl 2-chloropyrimidine-5-carboxylate (164 mg, 1.1 equiv), [1,1'-Bis(diphenylphosphino) ferrocene] dichloropalladium (II) complex with dichloromethane (18 mg, 0.03 equiv), and potassium carbonate (166 mg, 1.5 equiv) were added to the reaction mixture and the resulting suspension was stirred at 80° C. for 2 hours then allowed to stand at room temperature for 4 days. The reaction was partitioned between ethyl acetate (30 mL) and water (50 mL) and extracted with ethyl acetate (2×30 mL). The organic layer was separated, washed with brine (50 mL), dried over sodium sulfate, filtered, and concentrated to provide crude material that was purified by prep-TLC (5:1 petroleum ether: ethyl acetate) to afford ethyl 2-(5-((3-ethoxy-5-fluoropyridin-2-yl)oxy)pyridin-3-yl)pyrimidine-5-carboxylate (50 mg, 16%). MS (ES+) 385.0 (M+H).

Step 4: 2-(5-((3-Ethoxy-5-fluoropyridin-2-yl)oxy) pyridin-3-yl)pyrimidine-5-carboxylic Acid Sodium hydroxide (0.20 mL, 3.0 equiv, 2M) was added to ethyl 2-(5-((3-ethoxy-5-fluoropyridin-2-yl)oxy)pyridin-3-yl)pyrimidine-5-carboxylate (50 mg, 1.0 equiv) in ethanol (10 mL). The reaction was stirred at 25° C. for 16 hours. The solution was diluted with water (50 mL) and extracted with ethyl acetate (3×30 mL). The aqueous layer was acidified with hydrochloric acid (2N) to a pH of 3. The solution was extracted with ethyl acetate (15 mL), dried over sodium sulfate, and concentrated to yield 2-(5-((3-ethoxy-5-fluoropyridin-2-yl)oxy)pyridin-3-yl)pyrimidine-5-carboxylic acid (25 mg, 54%) as a yellow solid. MS (ES+) 357.0 (M+H).

Step 5: (S)-2-(5-((3-Ethoxy-5-fluoropyridin-2-yl) oxy)pyridin-3-yl)-N-(tetrahydrofuran-3-yl)pyrimidine-5-carboxamide The title compound was prepared according to general procedure A using 2-(5-((3-ethoxy-5-fluoropyridin-2-yl) oxy)pyridin-3-yl)pyrimidine-5-carboxylic acid (25 mg, 1.0 equiv) and (S)-tetrahydrofuran-3-amine (18.3 mg, 3.0 equiv). The crude material was purified by prep-HPLC to afford (S)-2-(5-((3-ethoxy-5-fluoropyridin-2-yl)oxy)pyridin-3-yl)-N-(tetrahydrofuran-3-yl)pyrimidine-5-carboxamide (20 mg, 67%) as a white solid. $^1H$ NMR (400 MHz, DMSO-d6) δ1.38 (t, 3H), 1.87-2.00 (m, 1H), 2.14-2.28 (m, 1H), 3.65 (dd, 1H), 3.70-3.79 (m, 1H), 3.83-3.94 (m, 2H), 4.21 (q, 2H), 4.46-4.56 (m, 1H), 7.65-7.74 (m, 2H), 8.37 (dd, 1H), 8.65 (d, 1H), 8.98 (d, 1H), 9.29 (s, 2H), 9.40 (d, 1H). MS (ES+) 425.9 (M+H).

Pharmacological Data

The following protocols may of course be varied by those skilled in the art.

Generation of Human DGAT2 (hDGAT2) Construct

A construct for hDGAT2 was generated with an N-terminal FLAG tag (an octapeptide with the amino acid sequence of AspTyrLysAspAspAspAspLys). For the FLAG-tagged hDGAT2 construct, the cDNA for hDGAT2 was custom-synthesized at Genscript and cloned into the pFastBac1 vector (Invitrogen) by using BamHI/XhoI restriction enzymes to generate an N-terminally FLAG-tagged pFastBac1-FLAG-hDGAT2 construct (amino acids 1-388). The construct was confirmed by sequencing in both directions.

DGAT2 Expression and Preparation of the DGAT2 Membrane Fraction

Recombinant baculovirus for the FLAG-tagged hDGAT2 was generated in SF9 insect cells using Bac-to-Bac baculovirus expression system (Invitrogen) according to the manufacturer's protocol. For the expression of hDGAT2, SF9 cells (20 L) grown in Sf900II media were infected with hDGAT2 baculovirus at a multiplicity of infection of 1 in a Wave Bioreactor System 20/50P wave bag (GE Healthcare). After 40 hours of infection, the cells were then harvested by centrifugation at 5,000× g. The cell pellets were washed by resuspending in phosphate buffered saline (PBS) and collected by centrifugation at 5,000× g. The cell paste was flash frozen in liquid $N_2$ and stored at −80° C. until needed. All operations below were at 4° C. unless otherwise noted. The cells were resuspended in lysis buffer (50 mM Tris-HCl, pH 8.0, 250 mM sucrose) including 1 mM ethylenediaminetetraacetic acid (EDTA) and the complete protease inhibitor cocktail (Roche Diagnostics) at a ratio of 3 ml buffer per 1 g cell paste. The cells were lysed by dounce homogenizer. The cell debris was removed by centrifugation at 1,000× g for 20 min, and the supernatant was centrifuged at 100,000× g for 1 hour. The resulting pellet was rinsed three times by filling ultracentrifuge tubes to the top with ice cold PBS before decanting. The washed pellet was resuspended with gentle stirring for 1 hour in lysis buffer containing 8 mM 3-[(3-cholamidopropyl)dimethylammonio]-1-propanesulfonate (CHAPS) at a ratio of 1 mL buffer per 1 g of original cell paste and centrifuged again at 100,000× g for 1 hour. The resulting supernatant was aliquotted, flash frozen in liquid $N_2$, and stored at −80° C. until use.

In Vitro DGAT2 Assay and Determination of $IC_{50}$ Values for DGAT2 Inhibitors

For determination of IC50 values, the reactions were carried out in 384-well white Polyplates (Perkin Elmer) in a total volume of 20 μL. To 1 μL of compounds dissolved in 100% DMSO and spotted at the bottom of each well, 5 μL of 0.04% bovine serum albumin (BSA) (fatty acid free, Sigma Aldrich) was added and the mixture was incubated at room temperature for 15 minutes. hDGAT2 membrane fractions were diluted in 100 mM Hepes-NaOH, pH 7.4, 20 mM $MgCl_2$ containing 200 nM methyl arachidonyl fluorophosphonate (Cayman Chemical; dried from ethyl acetate stock solution under argon gas and dissolved in DMSO as 5 mM stock). 10 μL of this enzyme working solution was added to the plates and incubation continued for 2 hours at room temperature. DGAT2 reactions were initiated by the addition of 4 μL of substrates containing 30 μM [1-$^{14}$C]decanoyl-CoA (custom-synthesized by Perkin Elmer, 50 mCi/mmol) and 125 μM 1,2-didecanoyl-sn-glycerol (Avanti Polar Lipids) dissolved in 12.5% acetone. The reaction mixtures were incubated at room temperature for 40 min and the reactions were stopped by addition of 5 μL of 1% $H_3PO_4$. After the addition of 45 μL MicroScint-E (Perkin-Elmer), plates were sealed with Top Seal-A covers (Perkin-Elmer) and phase partitioning of substrates and products was achieved using a HT-91100 microplate orbital shaker (Big Bear Automation, Santa Clara, CA). Plates were centrifuged at 2,000× g for 1 minute in an Allegra 6R Centrifuge (Beckman Coulter) and then were sealed again with fresh covers before reading in a 1450 Microbeta Wallac Trilux Scintillation Counter (Perkin Elmer). DGAT2 activity was measured by quantifying the generated product [$^{14}$C]tridecanoylglycerol in the upper organic phase.

Background activity obtained using 50 μM of (R)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone (WO 2013150416, Example 196-A) for complete inhibition of DGAT2 was subtracted from all reactions. Inhibitors were tested at eleven different concentrations to generate $IC_{50}$ values for each compound. The eleven inhibitor concentrations employed typically included 50, 15.8, 5, 1.58, 0.50, 0.16, 0.05, 0.016, 0.005, 0.0016, and 0.0005 μM. The data were plotted as percentage of inhibition versus inhibitor concentration and fit to the equation, $y=100/[1+(x/IC_{50})^z]$, where $IC_{50}$ is the inhibitor concentration at 50% inhibition and z is the Hill slope (the slope of the curve at its inflection point). Table 4 below provides the $IC_{50}$ values of the Examples for inhibition of DGAT2 in accordance with the above-described assay. Results are reported as geometric mean $IC_{50}$ values.

TABLE 4

$IC_{50}$ values of Examples for inhibition of DGAT2

| Example Number | DGAT2 $IC_{50}$ [nM] |
|---|---|
| 1 | 17.2 |
| 2 | 200 |
| 3.1 | 13.5 |
| 3.2 | 83.6 |
| 3.3 | 196 |
| 3.4 | 181 |
| 3.5 | 238 |
| 3.6 | 35.4 |
| 3.7 | 66.5 |
| 4 | 7.4 |
| 5 | 14.0 |
| 6a | 20.9 |
| 6b | 23.2 |
| 7 | 83.0 |
| 8 | 3.7 |

Determination of $IC_{50}$ Values for DGAT2 Inhibitors in Human Hepatocytes

For evaluation of the effects of DGAT2 inhibitors in a cell-based setting, cryopreserved human hepatocytes (Lot NON and EBS, Celsis, Chicago, IL) were thawed and plated onto type I collagen-coated plates according to the manufacturer's instructions. After 24 hours overnight recovery period, the cells were overlayed with media containing 250 μg/ml Matrigel (BD Biosciences, San Jose, CA). The following day, media was aspirated and replaced with serum-free Williams Media E (Life Technologies, Grand Island, NY) containing 400 μM sodium dodecanoate (Sigma-Aldrich, St. Louis, MO). Forty-five minutes later, a selective DGAT1 inhibitor (Example 3, WO2009016462, prepared as a 100× stocks in 25% DMSO, 75% Williams' Media E) was added to all wells at a final concentration (3 μM) that completely suppressed endogenous DGAT1 activity. DGAT2 inhibitors were then added to the desired final concentration. After a 15 minute preincubation, 0.2 μCi [1,3-$^{14}$C]-glycerol (American Radio Chemicals, St. Louis, MO) was added to each well followed by a 3 hour incubation. At this point the media was removed, the cells washed once with PBS and then lysed in isopropyl alcohol: tetrahydrofuran (9:1) prior to centrifugation at 3000 rpm for 5 minutes. Radiolabeled lipids were resolved using a 2-solvent system by thin layer chromatography with solvent 1 consisting of ethyl acetate: isopropyl alcohol: chloroform: methanol: 0.25% potassium chloride in water (100:100:100:40.2:36.1, v/v/v/v) and solvent 2 consisting of hexane: diethyl ether: acetic acid (70:27:3, v/v/v)). TLC plates were developed in solvent 1 one-third of the plate height, the plate dried under nitrogen and then developed to the plate top. After separation, radiolabeled lipids were visualized using a Molecular Dynamics' Phosphorlmager system. The half maximal inhibitory concentrations ($IC_{50}$ values) were determined using GraphPad Prism (GraphPad Software, Inc., La Jolla, CA) using Hill function with fixed baseline=0 (vehicle control) and Hill slope=1.

In this setting, Example 1 showed the geometric mean $IC_{50}$ value of 2.8 nM (N=10).

In Vivo Effects of DGAT2 Inhibitors on Plasma and Hepatic Triglyceride Levels

The rat western diet model was utilized to assess the longer term effects of the treatment with DGAT2 inhibitors on plasma triglyceride production and hepatic triglyceride content. Male Sprague-Dawley rats were housed under standard laboratory conditions on a 12-hour light, 12-hour dark cycle (lights on at 06:00). Two weeks prior to study start animals were placed on a high-fat, high-cholesterol diet (D12079b, Research Diets, New Brunswick, NJ). This diet provides ~43% of kilocalories from carbohydrate and ~41% of kilocalories from fat. DGAT2 inhibitors were administered orally as a solution (10 mL/kg dosing volume) in 0.5% HPMCAS-HF and 0.015% SLS in DI water, pH 8.5 (methylcellulose and butylated hydroxytoluene were obtained from Sigma-Aldrich, St. Louis, MO). Vehicle-treated animals received an aqueous solution of 0.5% HPMCAS-HF and 0.015% SLS in DI water, pH 8.5 alone. DGAT2 inhibitors were administered orally twice daily for 7 days at 08:00 and 16:00 at 1, 3, 10, 30 and 90 mg/kg. On day 8, all animals were fasted at 06:00, dosed with vehicle or DGAT2 inhibitors at 10:00 and sacrificed 2 hours post-dose. Rats were sacrificed by carbon dioxide asphyxiation and blood collected via lateral tail vein. Plasma TG levels were determined using a Roche Hitachi Chemistry analyzer according to the manufacturer's instructions (Roche Diagnostics Corporation, Indianapolis, IN) and data was analyzed using GraphPad Prism (GraphPad Software, Inc., La Jolla, CA). Livers sample collection for determination of hepatic triglyceride content was excised at time of sacrifice, immediately frozen in liquid nitrogen, and held at −80° C. until analysis. For assessment of tissue triglyceride levels a section of liver wrapped in aluminum foil was pulverized with a hammer, on an aluminum heat block in a liquid nitrogen bath. Pulverization of the liver tissue produced a homogeneous powder. Homogenization buffer, Tris pH 7.4, 98.9 milliliters 0.9% NaCl and 100 microliters of Triton X 100, was mixed on a stir plate for 10 minutes prior to using. Sample weights of approximately one-hundred milligrams of homogenous liver tissue were weighed and placed in Lysing Matrix D tube (MP Biomedicals, Cat #6913-100) with 1 mL of homogenization buffer. All samples were then placed in the FastPrep FP120 (MP Biomedicals, Cat #6001-120) for 2 minutes or until tissue was properly homogenized. All samples were then spun for 30 seconds at 10,000 g, to clear foam from homogenization. 50 microliters of sample was transferred to a sterile mixing plate with 450 microliters of Dulbeccos phosphate-buffered saline (DPBS) to create a 1:10 dilution. Upon re-suspension of the new sample, all samples were transferred to sampling tubes for the Siemens Advia XPT Clinical Analyzer. The triglyceride assay was performed through absorbance and reported as milligrams per deciliter. Triglycerides were then normalized per gram of tissue in Microsoft Excel.

Figure 3:
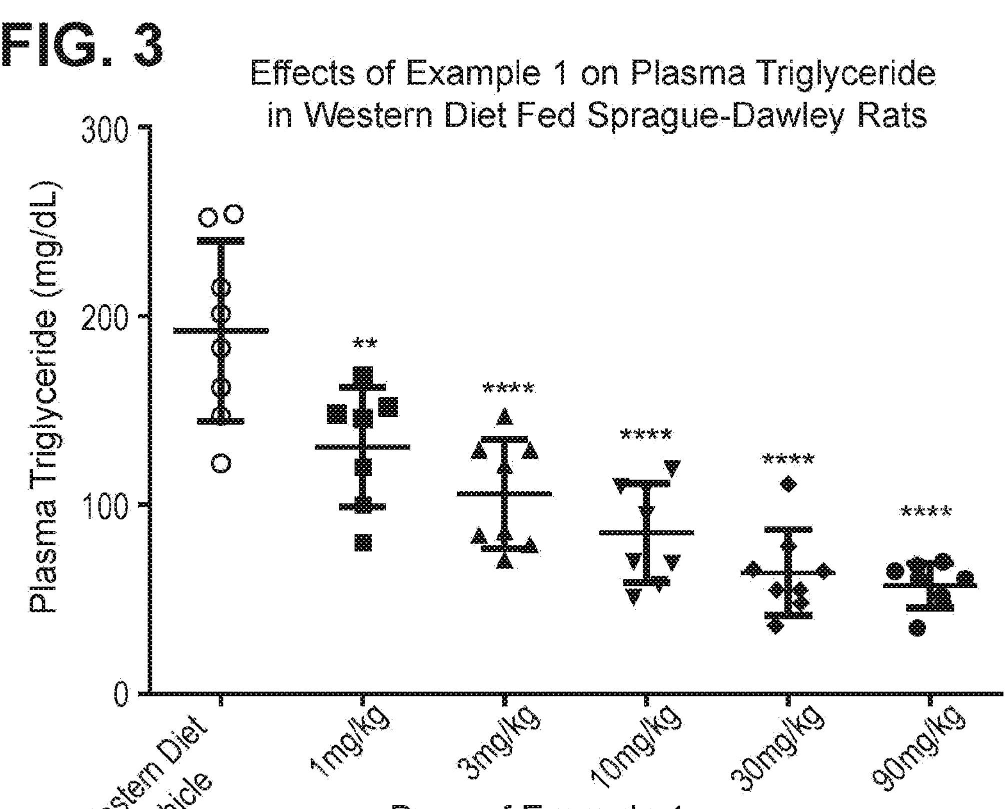
FIGS. 3 and 4 summarize the effects of oral administration with Example 1 on plasma and hepatic triglyceride levels in western diet fed Sprague Dawley rats respectively.
Figure 4:
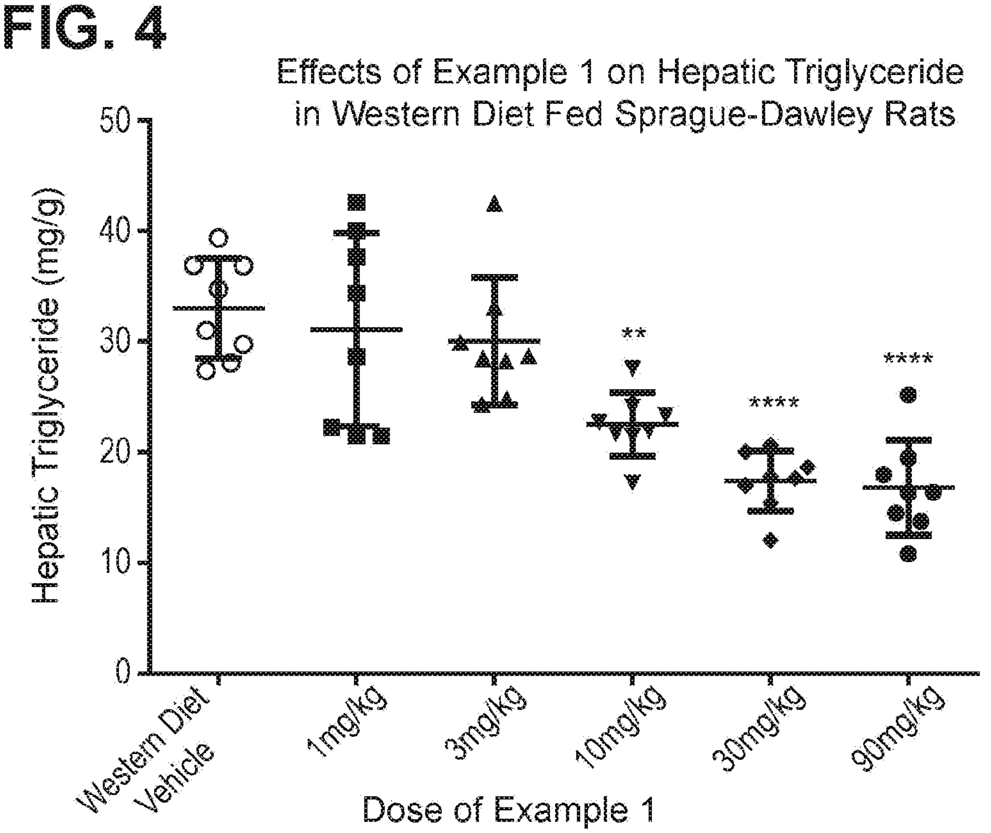

FIGS. 3 and 4 summarize the effects of oral administration with Example 1 on plasma and hepatic triglyceride levels in western diet fed Sprague Dawley rats in accordance with the above-described methods. Data are mean±standard deviation from 8 animals. Difference between group means relative to vehicle was performed by a 1-way ANOVA followed by a Dunnett's multiple comparisons test $^{}p<0.01$, $^{**}p<0.0001$.

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for reduction of triglyceride level in a human, wherein the method comprises a step of administering to the human in need of such reduction an effective amount of a compound of Formula (I) or a pharmaceutically acceptable salt of said compound, wherein the compound of Formula (I) is:

(I)

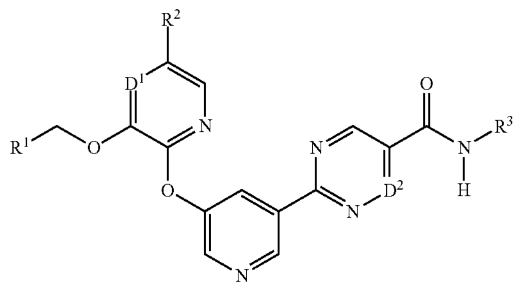

wherein $D^1$ and $D^2$ are each independently N or CH;

$R^1$ is H, or $(C_1\text{-}C_2)$alkyl optionally substituted with one or two substituents each independently selected from fluoro and $(C_3\text{-}C_6)$ cycloalkyl;

$R^2$ is H or fluoro;

$R^3$ is

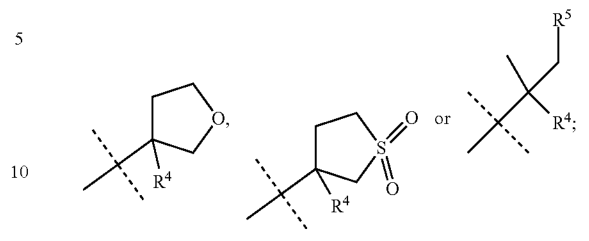

$R^4$ is H, cyano, or $(C_1\text{-}C_4)$alkyl optionally substituted with one or two substituents each independently selected from —OH and $—S(O)_2R^6$;

$R^5$ is H or —OH; and $R^6$ is $(C_1\text{-}C_4)$alkyl.

2. The method of claim 1 wherein the method reduces triglyceride level in plasma, liver, or a combination thereof of the human.

3. The method of claim 2 wherein the method reduces triglyceride level in liver of the human.

4. The method of claim 1 wherein the compound of Formula (I) is (I)

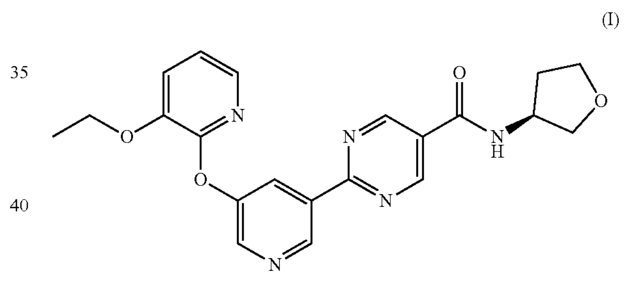

or a pharmaceutically acceptable salt thereof.

5. The method of claim 2 wherein the compound of Formula (I) is (I)

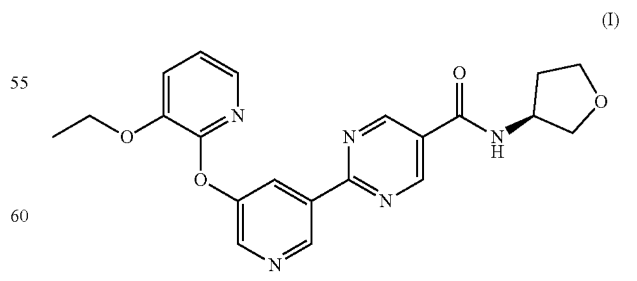

or a pharmaceutically acceptable salt thereof.

6. The method of claim 3 wherein the compound of Formula (I) is (I)

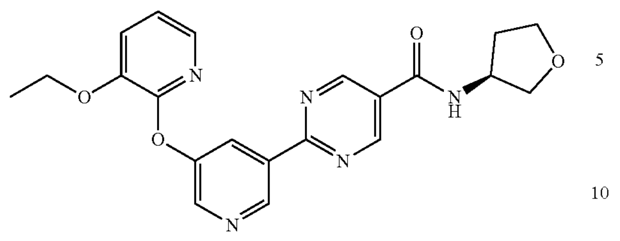

or a pharmaceutically acceptable salt thereof.

7. The method of claim 1 wherein the compound of Formula (I) is (I)

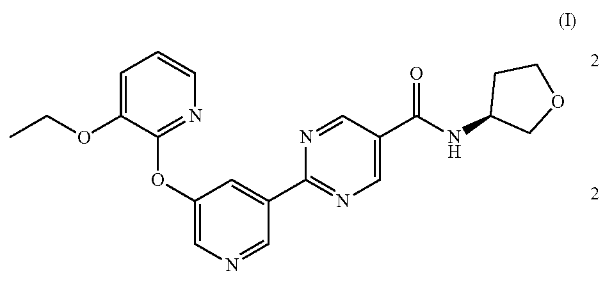

8. The method of claim 2 wherein the compound of Formula (I) is (I)

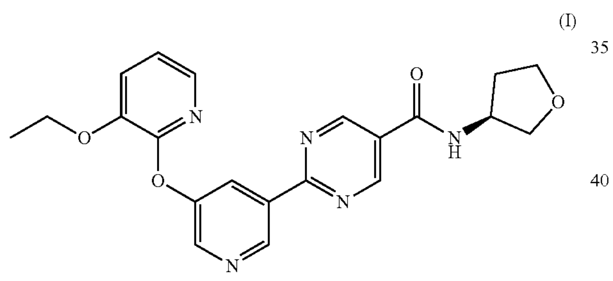

9. The method of claim 3 wherein the compound of Formula (I) is (I)

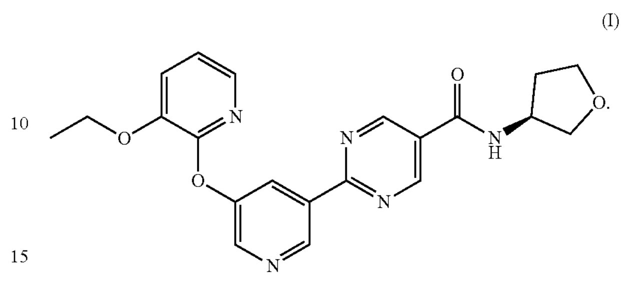

10. The method of claim 1 wherein the compound of Formula (I) is 2-(5-((3-ethoxypyridin-2-yl)oxy)pyridin-3-yl)-N-(tetrahydrofuran-3-yl)pyrimidine-5-carboxamide or a pharmaceutically acceptable salt thereof.

11. The method of claim 2 wherein the compound of Formula (I) is 2-(5-((3-ethoxypyridin-2-yl)oxy)pyridin-3-yl)-N-(tetrahydrofuran-3-yl)pyrimidine-5-carboxamide or a pharmaceutically acceptable salt thereof.

12. The method of claim 3 wherein the compound of Formula (I) is 2-(5-((3-ethoxypyridin-2-yl)oxy)pyridin-3-yl)-N-(tetrahydrofuran-3-yl)pyrimidine-5-carboxamide or a pharmaceutically acceptable salt thereof.

13. The method of claim 1 wherein the compound of Formula (I) is 2-(5-((3-ethoxypyridin-2-yl)oxy)pyridin-3-yl)-N-(tetrahydrofuran-3-yl)pyrimidine-5-carboxamide.

14. The method of claim 2 wherein the compound of Formula (I) is 2-(5-((3-ethoxypyridin-2-yl)oxy)pyridin-3-yl)-N-(tetrahydrofuran-3-yl)pyrimidine-5-carboxamide.

15. The method of claim 3 wherein the compound of Formula (I) is 2-(5-((3-ethoxypyridin-2-yl)oxy)pyridin-3-yl)-N-(tetrahydrofuran-3-yl)pyrimidine-5-carboxamide.

* * * * *